United States Patent
Dahners

(10) Patent No.: US 8,764,764 B2
(45) Date of Patent: Jul. 1, 2014

(54) SURGICAL PLATE PULLER DEVICES AND METHODS FOR USE WITH SURGICAL BONE SCREW/PLATE SYSTEMS

(75) Inventor: Laurence E. Dahners, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 565 days.

(21) Appl. No.: 11/818,057

(22) Filed: Jun. 13, 2007

(65) Prior Publication Data

US 2008/0234752 A1 Sep. 25, 2008

Related U.S. Application Data

(63) Continuation-in-part of application No. 11/726,382, filed on Mar. 21, 2007.

(51) Int. Cl.
*A61B 17/58* (2006.01)
*A61B 17/88* (2006.01)

(52) U.S. Cl.
USPC .......................................... 606/104; 606/291

(58) Field of Classification Search
USPC ......... 606/104, 280, 281, 289, 291, 305, 293, 606/295, 296, 300, 322
See application file for complete search history.

(56) References Cited

U.S. PATENT DOCUMENTS

| 132,946 A | 11/1872 | Armstrong |
| 1,116,532 A * | 11/1914 | Armstrong ..................... 81/453 |
| 1,498,040 A | 6/1924 | Johnson |
| 1,785,847 A | 12/1930 | Valentine |
| 2,248,054 A * | 7/1941 | Becker ............................ 81/457 |
| 2,507,882 A | 5/1950 | Berman |
| 4,877,020 A | 10/1989 | Vich |
| 5,667,513 A * | 9/1997 | Torrie et al. .................. 606/104 |
| 5,702,398 A * | 12/1997 | Tarabishy ..................... 606/232 |
| 5,709,686 A | 1/1998 | Talos et al. |

(Continued)

FOREIGN PATENT DOCUMENTS

| CN | 2008/80017163.3 | 8/2010 |
| CN | 2010/072800361660 | 8/2010 |

(Continued)

OTHER PUBLICATIONS

International Search Report and Written Opinion dated Oct. 6, 2008.

(Continued)

*Primary Examiner* — Christian Sevilla
(74) *Attorney, Agent, or Firm* — Jenkins, Wilson, Taylor & Hunt, P.A.

(57) ABSTRACT

A plate puller device can include a head portion and extension rod portion. The device enables the fastener receiving member to be pulled against a bone surface before a head section of the fastener is advanced within the fastener receiving member into a locked position. The head portion can be positioned between the head section of the fastener and a surface of the fastener receiving member not adjacent to the bone surface. Also, a plate puller device can include a screwdriver, a grasper portion and a grasper sleeve. The grasper portion and grasper sleeve can be threadingly mated wherein rotation of the grasper sleeve forces a head portion of the grasper portion to grip the head section of the fastener to prevent the head section from advancing within the fastener receiving member.

3 Claims, 22 Drawing Sheets

(56) References Cited

U.S. PATENT DOCUMENTS

| | | | |
|---|---|---|---|
| 6,183,472 B1 | 2/2001 | Lutz | |
| 6,206,881 B1 | 3/2001 | Frigg et al. | |
| 6,306,140 B1 | 10/2001 | Siddiqui | |
| 6,322,562 B1 | 11/2001 | Wolter | |
| 6,342,055 B1 | 1/2002 | Eisermann et al. | |
| 6,361,537 B1 | 3/2002 | Anderson | |
| 6,454,769 B2 | 9/2002 | Wagner | |
| 6,592,586 B1 | 7/2003 | Michelson | |
| 6,701,812 B1 * | 3/2004 | Sawamura | 81/453 |
| 6,827,722 B1 * | 12/2004 | Schoenefeld | 606/104 |
| 6,860,889 B2 * | 3/2005 | Bonati et al. | 606/104 |
| 6,955,677 B2 | 10/2005 | Dahners | |
| 6,981,974 B2 | 1/2006 | Berger | |
| 6,997,086 B1 * | 2/2006 | Graham | 81/451 |
| 7,527,639 B2 | 5/2009 | Orbay et al. | |
| 7,780,711 B2 | 8/2010 | Orbay et al. | |
| 2003/0120277 A1 | 6/2003 | Berger | |
| 2004/0073218 A1 * | 4/2004 | Dahners | 606/69 |
| 2004/0158258 A1 * | 8/2004 | Bonati et al. | 606/104 |
| 2004/0260291 A1 | 12/2004 | Jensen | |
| 2005/0149031 A1 | 7/2005 | Ciccone et al. | |
| 2005/0165400 A1 | 7/2005 | Fernandez | |
| 2005/0222575 A1 | 10/2005 | Ciccone et al. | |
| 2006/0009771 A1 | 1/2006 | Orbay et al. | |
| 2006/0100626 A1 | 5/2006 | Rathbun et al. | |
| 2007/0162018 A1 | 7/2007 | Jensen et al. | |
| 2008/0234677 A1 | 9/2008 | Dahners | |
| 2008/0234749 A1 * | 9/2008 | Forstein | 606/291 |
| 2008/0234752 A1 | 9/2008 | Dahners | |

FOREIGN PATENT DOCUMENTS

| | | |
|---|---|---|
| CN | 2008/800171633 | 12/2012 |
| DE | 4343117 A1 | 6/1995 |
| EP | 0530585 | 3/1993 |
| EP | 1 741 397 | 1/2007 |
| FR | 2 876 270 | 4/2006 |
| WO | WO 2006/037898 | 4/2006 |
| WO | WO2006/124987 | 11/2006 |
| WO | WO 2006/124987 A1 | 11/2006 |
| WO | WO 2006124987 A1 * | 11/2006 |

OTHER PUBLICATIONS

International Search Report and Written Opinion dated Jul. 11, 2008.
Office Action for Japanese Application No. 2009-554517 dated Oct. 16, 2012.
European Office Action for Application No. 08 725 277.1-1506 dated Mar. 7, 2013.
Non-Final Office Action for U.S. Appl. No. 11/726,382 dated Dec. 13, 2013.
Israeli Office Action for IL Application No. 201056 dated Dec. 18, 2013.
First Office Action for Chinese Application No. 200880017163.3 dated Mar. 15, 2011.
Second Office Action for Chinese Application No. 200880017163.3 dated Apr. 1, 2012.
Israeli Office Action for IL Application No. 201056 dated Apr. 30, 2012.
Examination Report for Australian Application Serial No. AU 2008227127 dated Jul. 24, 2012.
Non-Final Office Action from U.S. Appl. No. 11/726,382 dated Jul. 6, 2009.
European Patent Office Notice of Publication for EP 08725277.1 dated Dec. 16, 2009.
International Preliminary Report on Patentability for PCT/US2008/007259 dated Dec. 17, 2009.
Final Office Action from U.S. Appl. No. 11/726,382 dated Apr. 5, 2010.
Extended European Search Report for Application Serial No. EP 08 72 5277 dated Jul. 2, 2012.
Notification to Grant for Chinese Application No. CN 2008/80017163 dated Aug. 3, 2012.

* cited by examiner

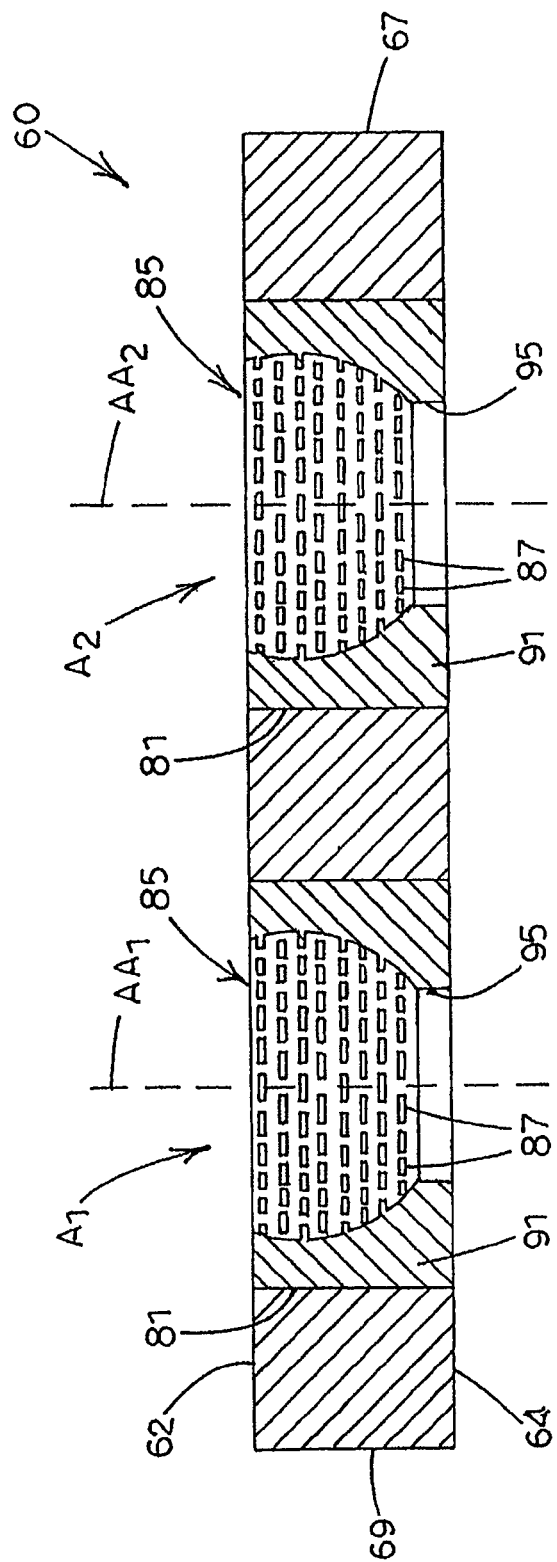

SURGICAL PLATE PULLER DEVICES AND METHODS FOR USE WITH SURGICAL BONE SCREW/PLATE SYSTEMS

RELATED APPLICATIONS

This application is a continuation-in-part of and claims priority to U.S. patent application Ser. No. 11/726,382, filed Mar. 21, 2007, the disclosure of which is incorporated herein by reference in its entirety.

TECHNICAL FIELD

The present disclosure relates generally to devices for pulling a fastener receiving member against a surface to which the fastener receiving member is meant to abut. A specific application of the present disclosure relates to the use of plate pulling devices with bone screw/plate systems in the course of orthopaedic surgical procedures.

BACKGROUND

A variety of techniques exist in the field of orthopaedic surgery for treating bone fractures. Many known techniques utilize bone screws and bone fixation plates. Typically, the plate is used to stabilize the site of a bone fracture, and one or more bone screws are inserted through apertures of the plate and threaded into the bone material so as to secure the plate to the bone material. It is also known that bone screw/plate systems can be improved by machining a thread onto the head of the bone screw, in addition to the thread normally machined onto the main shaft of the screw. In connection with the use of threaded-head screws, the apertures of the plate are threaded to matingly receive the threads of the screw head. Thus, as the screw is inserted into an aperture of the plate and threaded into the bone material, the head of the screw likewise is threaded into the aperture. As a result, the screw becomes rigidly affixed to the plate, in effect locking to the plate rather than simply bearing against the plate. Examples of threaded-head bone screws and threaded-aperture bone plates are disclosed in U.S. Pat. No. 5,709,686 to Talus et al.; U.S. Pat. No. 6,206,881 to Frigg et al.; and U.S. Pat. No. 6,306,140 to Siddiqui.

The use of threaded-head screws and threaded-aperture plates provides certain advantages. It is known that some types of small bone fragments tend to change position relative to the plate over time. This deleterious condition can result from the "toggling" of the screws affixed to the plate. However, when multiple screws are rigidly fixed to the plate by mating the respective threads of the screw heads with the threads of the corresponding plate apertures, the screws do not toggle in the plate. The locking action provided by the threaded-head screw in combination with the threaded-aperture plate prevents motion between the bone fragment and the plate as well as premature loosening of the screws.

Although the use of threaded-head screws has provided improvements in orthopaedic surgical techniques, there remains the disadvantage that these screw/plate systems are unidirectional. That is, the thread formed on the inside surface of the aperture of the plate is structurally fixed at a constant helical angle with respect to the central axis passing through the center point of the aperture. Hence, the head of a conventional threaded-head screw can only be rigidly affixed to the plate by mating its thread with that of the aperture, such that the bone screw is always inserted and threaded in one direction, e.g., perpendicularly or coaxially with respect to the plate.

Recent developments in this field provide screw/plate systems that allow the surgeon to choose the angle at which the screw is inserted through, and rigidly affixed in, an aperture of the plate. Examples of such systems are disclosed in U.S. Pat. No. 6,955,677 to Dahners. Such improvements enable the surgeon to direct the bone screw toward bone fragments that are not situated directly beneath the aperture of the plate, and also provide flexibility in the placement of the plate in relation to the bone fracture. These systems, however, do not address the possibility of the plate failing to completely pull against a bone surface before the head of the bone screw locks into the aperture of the plate, thereby leaving a gap between the plate and the bone surface to which the plate is intended to firmly abut. This is problematic in that the plate fails to perform its intended function, providing support for the bone fracture.

It would therefore be advantageous to provide a plate puller device that prevents the head section of the bone screw from advancing and locking within the aperture of the plate until the plate is pulled against the bone surface.

SUMMARY

According to the present disclosure, novel plate puller devices and methods are provided for preventing the head section of a bone screw from advancing within the aperture of the plate until the plate abuts the bone surface.

It is therefore an object of the present disclosure to provide plate puller devices and methods for providing improved implantation of a bone plate such that the plate is pulled against a bone surface.

An object having been stated hereinabove, and which is achieved in whole or in part by the subject matter disclosed herein, other objects will become evident as the description proceeds when taken in connection with the accompanying drawings as best described hereinbelow.

BRIEF DESCRIPTION OF THE DRAWINGS

A full and enabling disclosure of the present subject matter including the best mode thereof to one of ordinary skill in the art is set forth more particularly in the remainder of the specification, including reference to the accompanying figures in which:

FIG. 2B is a vertical cross-sectional side view of the fastener receiving member illustrated in FIG. 2A taken along cut-away line 2B-2B in FIG. 2A;

DETAILED DESCRIPTION

Reference will now be made in detail to presently preferred embodiments of the present subject matter, one or more examples of which are shown in the figures. Each example is provided to explain the subject matter and not as a limitation. In fact, features illustrated or described as part of one embodiment can be used in another embodiment to yield still a further embodiment. It is intended that the present subject matter cover such modifications and variations.

Figure 1:
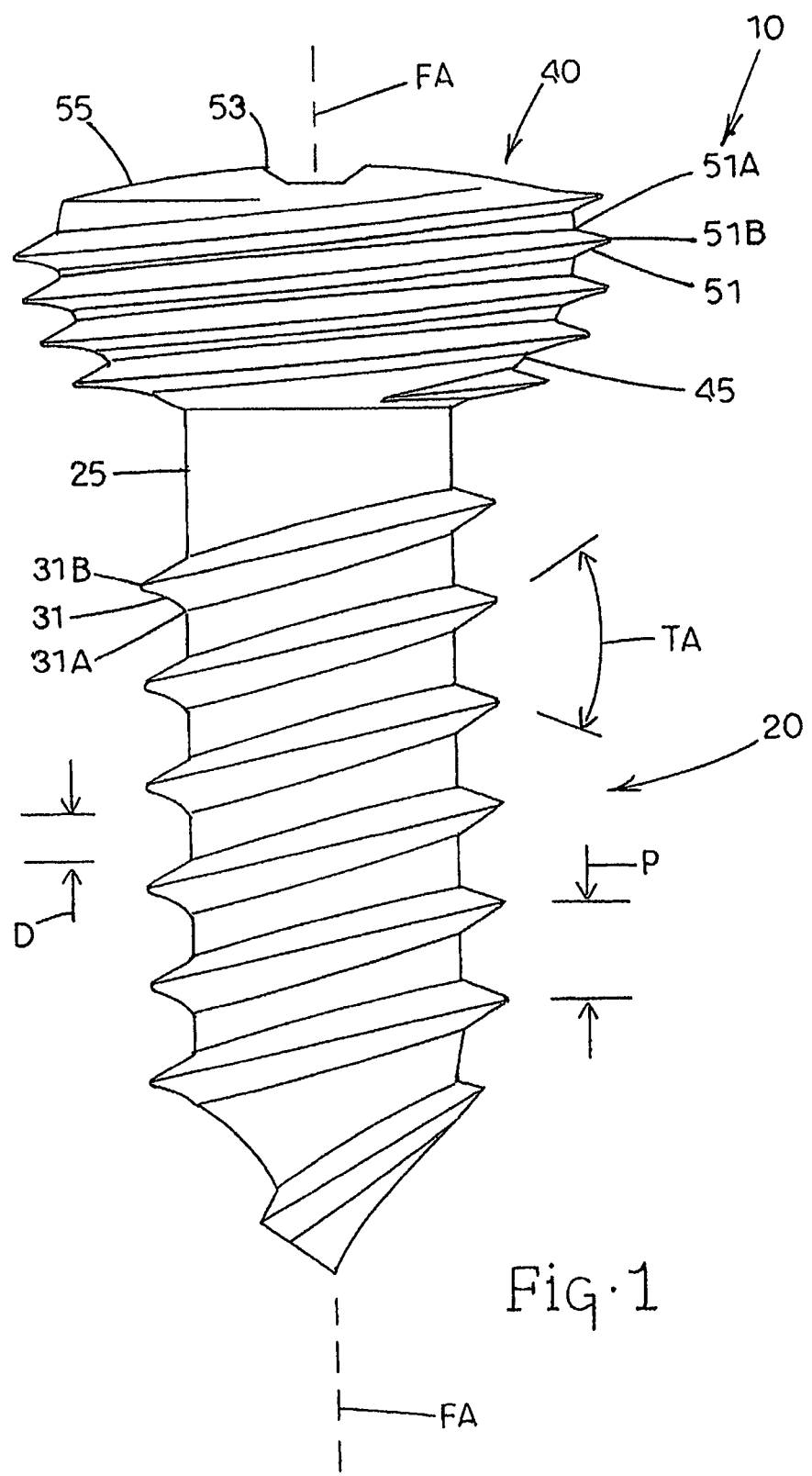
FIG. 1 is an elevation view of a fastener provided in accordance with the present disclosure.

Referring now to FIG. 1, one example of a threaded-head fastener, generally designated 10, is illustrated in accordance with the present disclosure. Fastener 10 can be constructed from any material appropriate for withstanding compressive, tensile, torque, or other forces encountered during and after application of fastener 10 to a target site. In the context of orthopaedic surgery, fastener 10 is preferably constructed from a biocompatible metal or metal alloy such as stainless steel, titanium, chromium, or alloys thereof. As is appreciated by persons skilled in the art, fastener 10 could also be constructed from a suitable ceramic material or a polymeric material such as a resorbable polymer, or could be coated with a polymeric film. Fastener 10 comprises an elongate section, generally designated 20, and an adjoining head section, generally designated 40, both of which are generally arranged along a longitudinal fastener axis FA. Elongate section 20 comprises a shaft having a first outer surface 25 coaxially disposed in relation to fastener axis FA. Preferably, first outer surface 25 is cylindrical. Elongate section 20 is machined to form a first thread 31 thereon. First thread 31 has a root 31A adjoining first outer surface 25 from which first thread 31 extends generally radially outwardly to terminate at a crest 31B. First thread 31 winds around first outer surface 25 or a length thereof in a generally helical fashion. In the illustrated example, first thread 31 has a conical or "V" cross-sectional profile and thus tapers from first outer surface 25 to its crest 31B.

In a one embodiment of the disclosure in which fastener 10 is utilized as a bone screw for anchoring to bone material B such as a bone fragment, the illustrated "V" profile of first thread 31 is advantageous in that renders fastener 10 self-tapping. The present disclosure, however, is not limited to any particular design for first thread 31. For instance, the profile of first thread 31 could be rectilinear or square, with its crest 31B being a generally flat surface. Alternatively, the profile of first thread 31 could be trapezoidal (i.e., an "Acme" thread). The degree of sharpness or flatness of crest 31B is not limited, and crest 31B could be rounded. Moreover, the present disclosure is not limited to any particular diameter of first outer surface 25, diameter of crest 31B, thread angle TA between the side walls of adjacent thread passes, or thread pitch P (i.e., the axial distance between the crest portions of adjacent thread passes, or the reciprocal of the number of thread passes per inch). Additionally, first thread 31 could be a multiple-threaded or multi-start design, in which two or more individual threads are cut beside each other. First thread 31 could also constitute one or more single threads formed on different axial sections of shaft. Also, pitch P of first thread 31 could be such that adjacent thread passes are separated from each other by an axial distance D over which only first outer surface 25 of shaft exists. Finally, the "hand" or "sense" associated with the turning of first thread 31 about fastener axis FA may or may not follow the standard right-hand rule.

Figure 4:
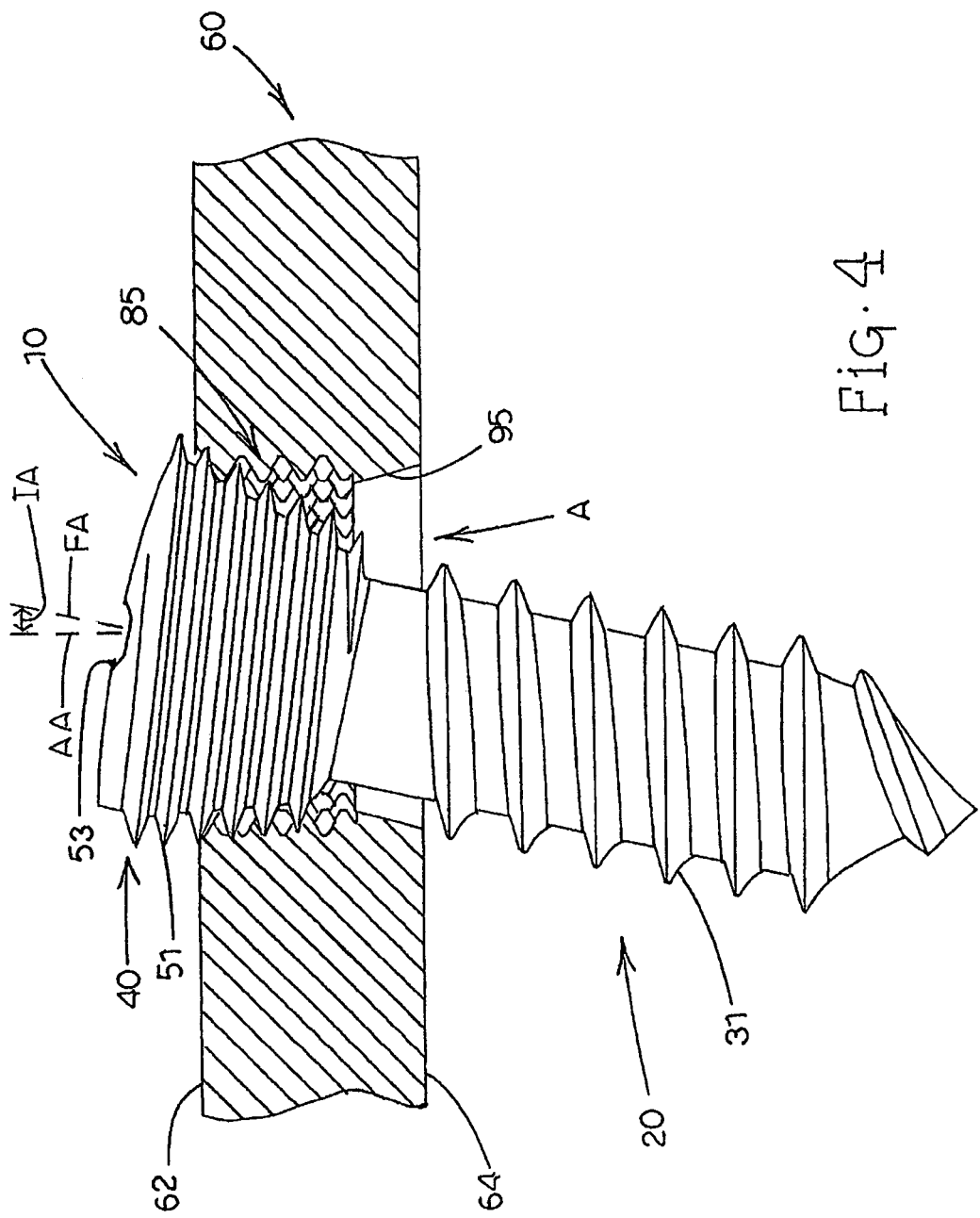
FIG. 4 is a partially cut away and vertical cross-sectional view of a fastener and fastener receiving member according to an alternative embodiment of the present disclosure.
Figure 5:
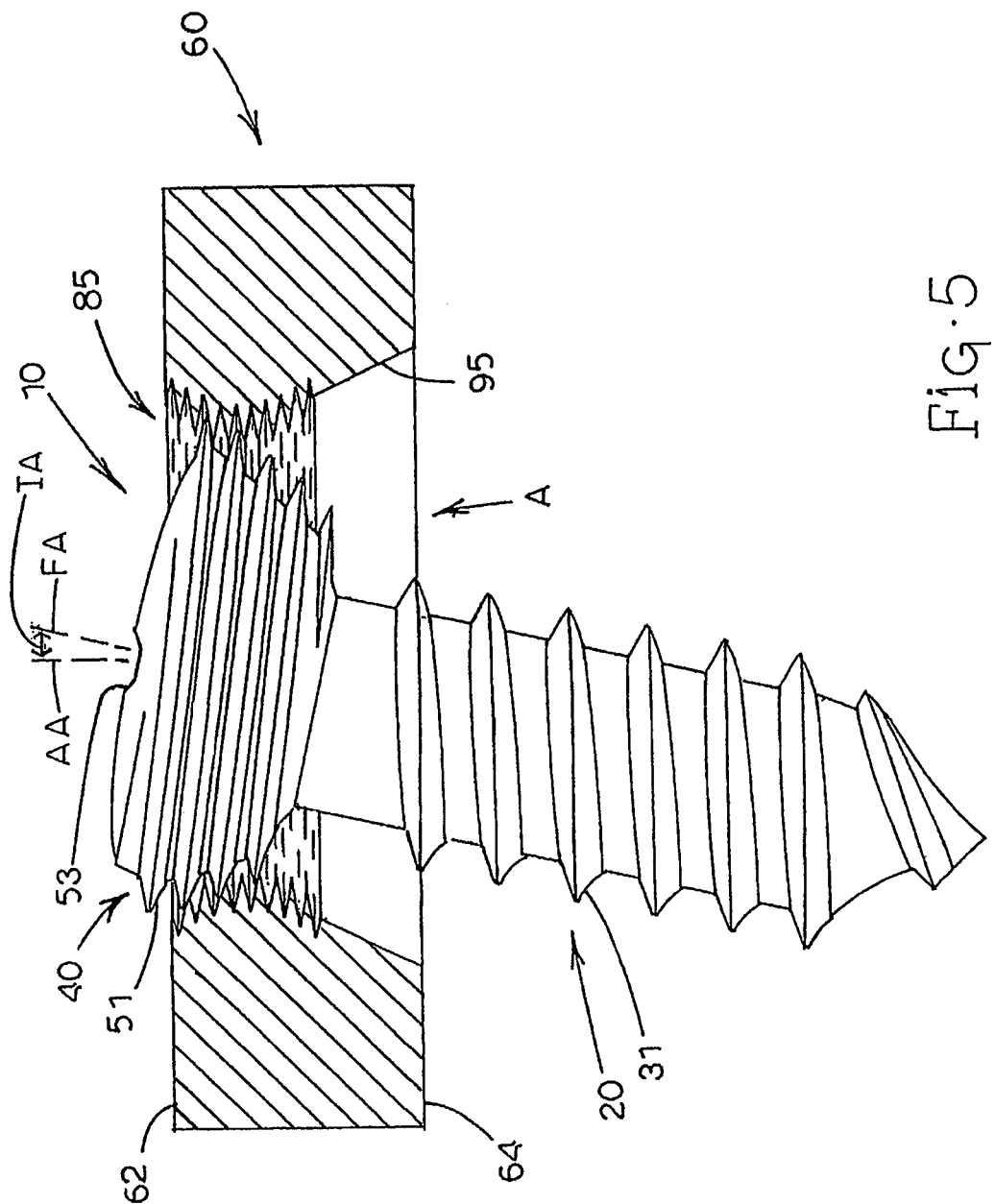
FIG. 5 is a partially cut away and vertical cross-sectional view of a fastener and fastener receiving member according to another alternative embodiment of the present disclosure.

With continuing reference to FIG. 1, head section 40 comprises a second outer surface 45 coaxially disposed in relation to fastener axis FA. In the example illustrated in FIG. 1, the shape of head section 40, i.e., the cross-sectional profile of second outer surface 45, is substantially hemispherical or parabolic. It will be understood, however, that head section 40 can have other types of rounded shapes, and its profile can be either convex or concave. Moreover, the shape of head section 40 can be substantially frusto-conical as shown in FIGS. 4 and 5. In addition, the shape of head section 40 can be a composite form, such as a converging/diverging or "trumpet-shaped" profile. Head section 40 is machined to form a second thread 51 thereon. Second thread 51 has a root adjoining second outer surface 45 from which second thread 51 extends generally radially outwardly to terminate at a crest 51B. Second thread 51 winds around second outer surface 45 in a generally helical fashion. To facilitate the turning of fastener 10 by the user thereof, a recess 53 is formed in a top surface 55 of head section 40 for the insertion of an appropriate tool such as a screwdriver, key, or wrench. The shape of recess 53 can be a single or cross-shaped slot, a square, a hexagon, a star, or the like.

In the illustrated example, second thread 51 has a conical or "V" profile and thus tapers from second outer surface 45 to crest 51B. The "V" profile of second thread 51 is preferred because it facilitates the self-tapping of head section 40 into a plate or other fastener receiving member 60 (see, e.g., FIGS. 2A and 2B), in accordance with the present disclosure and as described below. However, like first thread 31 of elongate section 20, the present disclosure is not limited to any particular design for second thread 51. Thus, no limitations are made with regard to the profile or shape of first thread 31, the degree of sharpness or flatness of its crest 31B, the outer diameter of any portion of second outer surface 45 or crest 31B (although the average diameter of head section 40 is greater than that of elongate section 20), the thread angle TA, the thread pitch P, the number and locations of the threads constituting second thread 51, or the turning direction of second thread 51 with respect to fastener axis FA.

In an alternative embodiment, elongate section 20 is not threaded, and fastener 10 takes the form of a peg or a pin. This alternative embodiment may be preferred in certain procedures where, for instance, the main object is to prevent tilting of a bone segment, as well as other procedures where there is no concern of fastener 10 pulling out from the bone and hence no need for elongate section 20 to be threaded. In these implementations, head section 40 is threaded, and thus the advantages and benefits of the present disclosure as described herein apply.

Turning to FIGS. 2A-2D, a fastener receiving member, generally designated 60, is illustrated in accordance with the present disclosure. In the illustrated example, fastener receiving member 60 is provided in the form of a mounting plate, such as a bone plate for use in orthopaedic surgical procedures. Fastener receiving member 60 can be constructed from any material appropriate for withstanding compressive, tensile, torque, or other forces encountered during and after application of fastener 10 to fastener receiving member 60 at a target site. In the context of orthopaedic surgery, fastener receiving member 60 is preferably constructed from a biocompatible metal or metal alloy such as stainless steel, titanium, cobalt, chromium, tungsten, tantalum, molybdenum, gold, and alloys thereof. Alternatively, fastener receiving member 60 can be constructed from a suitable ceramic or polymeric material. The polymeric material may be reinforced with glass, carbon, or metal fibers.

Fastener receiving member 60 comprises a first major outer surface 62, an opposing second major outer surface 64, and outer lateral edges 66, 67, 68 and 69 at the perimeter. In orthopaedic applications, second outer surface 64 can in some cases be used for contact with bone material B (see FIG. 3), while in other cases actual contact is unnecessary or undesirable. While in the illustrated example first and second outer surfaces 62 and 64 are planar, it will be understood that the cross-section of fastener receiving member 60 or certain portions thereof can have a contoured profile. For instance, in some types of orthopaedic applications, minimum contact between fastener receiving member 60 and the target bone material B might be desired. In such a case, second outer surface 64 or a portion thereof can be convex.

One or more apertures, generally designated A (e.g., apertures $A_1$ and $A_2$ shown in FIGS. 2A and 2B), are formed through the thickness of fastener receiving member 60 for receiving one or more elongate sections 20 of corresponding fasteners 10 therethrough. Each aperture A is defined by an inside surface 81 cut through the thickness of fastener receiving member 60. Each aperture A is generally transversely oriented in relation to first and second outer surfaces 62 and 64, and thus is generally coaxially disposed about a central aperture axis AA (e.g., aperture axis $AA_1$ or $AA_2$ shown in FIG. 2B) directed through the thickness of fastener receiving member 60. The precise number and arrangement of such apertures A can depend on the intended use for fastener receiving member 60. It will be understood, however, that the present disclosure contemplates procedures in which a multi-apertured fastener receiving member 60 is employed in connection with a single fastener 10, with one aperture A of such fastener receiving member 60 being selected by the user for interfacing with the single fastener 10.

Figure 3:
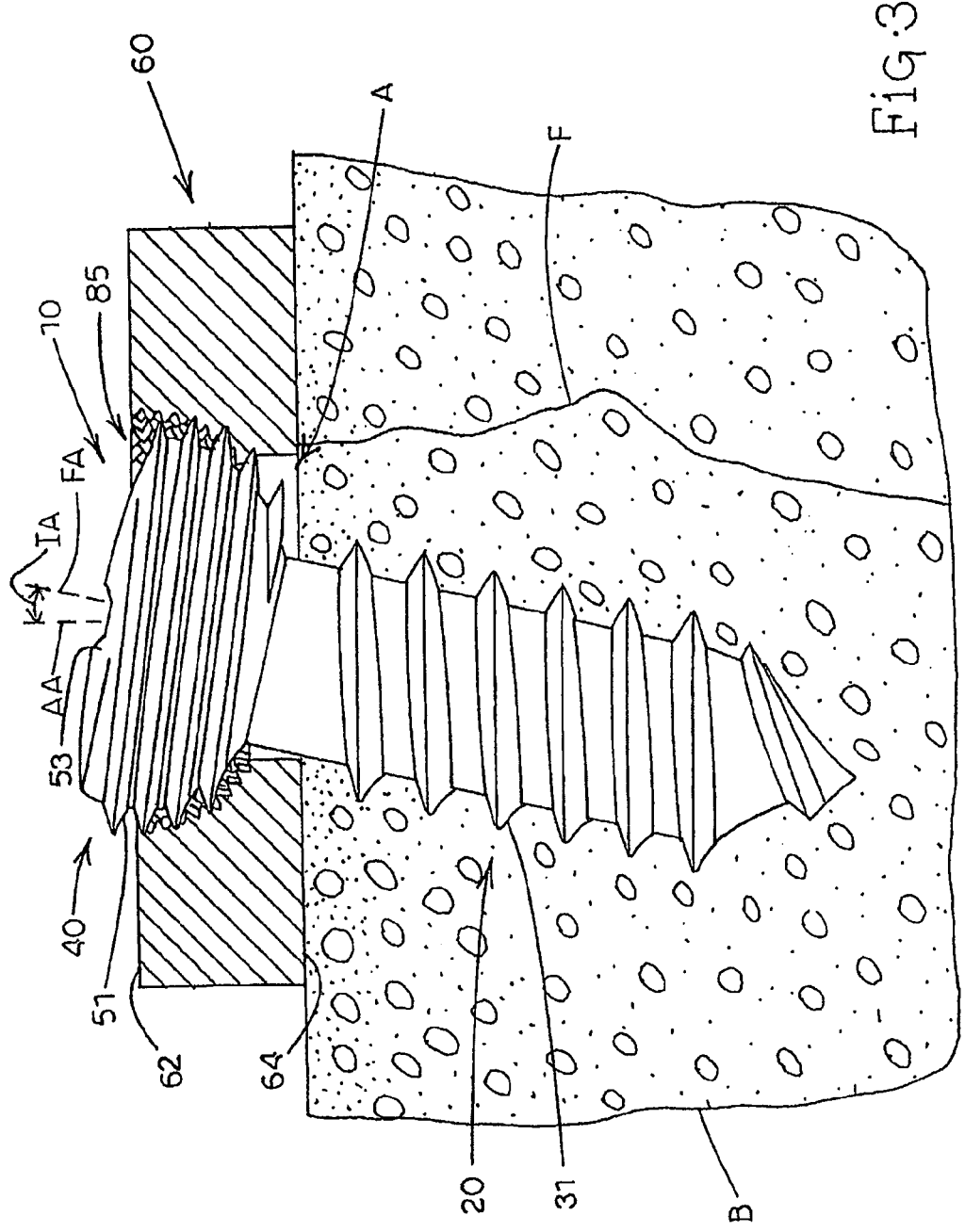
FIG. 3 is a partially cut away and vertical cross-sectional view illustrating an application of the present disclosure in which the fastener is affixed to the fastener receiving member and anchored to an object such as bone material at a desired insertion angle.

As indicated above, the present disclosure departs from the conventional use of a thread formed on inside surface 81 of aperture A for mating with the thread of a screw head. That is, apertures A of fastener receiving member 60 do not contain a permanent helical thread structure of fixed orientation. Instead, a tappable contact region, generally designated 85, is disposed on each inside surface 81 of fastener receiving member 60. The term "tappable" is used herein to denote that contact region 85 is structured such that it can be tapped by second thread 51 of head section 40 of fastener 10 in response to forceful insertion and rotation of head section 40 into the material of contact region 85. As described below in connection with FIG. 3, this enables the user to manipulate second thread 51 of head section 40 to form, in effect, a custom internal thread in contact region 85 sufficient to maintain fastener 10 at an arbitrary orientation in relation to receiving member 60 selected by the user. In FIG. 3, this orientation is represented by an insertion angle IA, defined between fastener axis FA and aperture axis AA. In accordance with the present disclosure, insertion angle IA can range from 0 to 90 degrees wherein at 0 degrees fastener axis FA coincides with aperture axis AA. Due to the relative positions of aperture A, second outer surface 64 and fastener 10, insertion angle IA in practice will be less than 90 degrees.

Figure 2A:
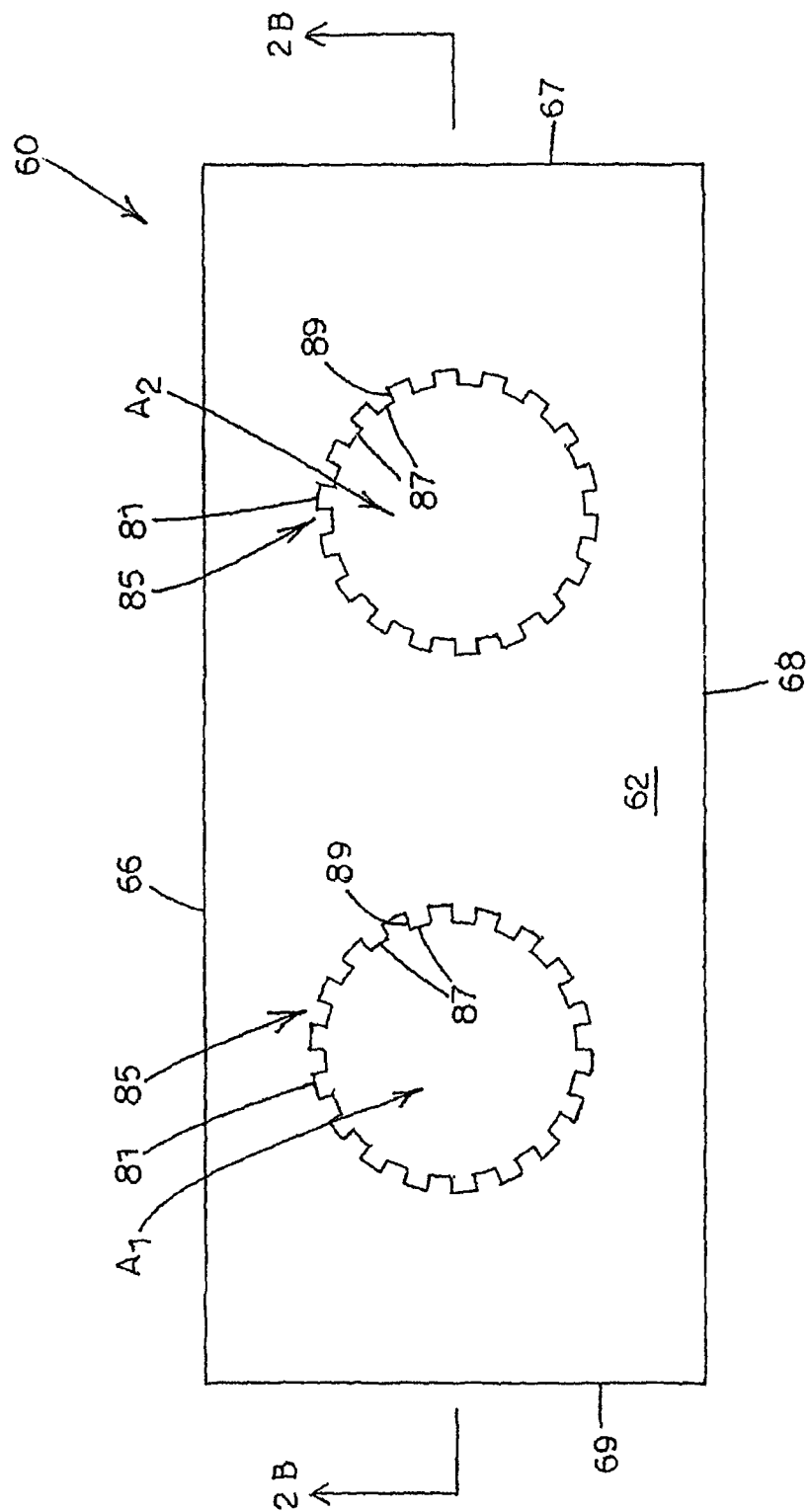
FIG. 2A is a top plan view of a fastener receiving member provided in accordance with the present disclosure.

In the embodiment illustrated in FIGS. 2A-2D, the tappable property is realized by structuring contact region 85 as a matrix of protrusions 87 and interstices 89 between protrusions 87. Protrusions 87 can be provided in any protruding form, such as pegs, bristles or tines. Protrusions 87 are based on inside surface 81 and extend generally radially inwardly into the open space of apertures A. Protrusions 87 can be formed directly from inside surface 81 and the region of fastener receiving member 60 circumscribing aperture A. Alternatively, as shown in FIG. 2B, protrusions 87 can be formed on a substrate 91 (see FIG. 2B) that is thereafter fitted to inside surface 81 as an insert, such as by press-fitting or binding. The material selected for protrusions 87 can be any material suitable for tapping by fastener 10. Non-limiting examples include stainless steel, titanium, cobalt, chromium, tungsten, tantalum, molybdenum, gold, and alloys thereof, as well as suitable polymers.

It will be noted that the density of protrusions 87 over the area of inside surface 81, and the size of individual protrusions 87, are not limited by the present disclosure, so long as the matrix formed on inside surface 81 renders contact region 85 tappable. Accordingly, the matrix of protrusions 87 can appear as a bristle board or a porous surface. The characteristic cross-sectional dimension of each protrusion 87 (e.g., diameter, width, or the like) can range from approximately 1 micron to approximately 25 mm, although the present disclosure is not limited to this range. The density of protrusions 87 over the area of inside surface 81 from which they protrude can range from approximately 5 to approximately 65%, although the present disclosure is not limited to this range. Protrusions 87 can be formed by any suitable means, such as growing protrusions 87 by material deposition, forming protrusions 87 by coating, welding protrusions 87 to inside surface 81, or forming ridges or grooves and subsequently cutting transversely through the ridges to discretize the ridges into protrusions 87.

Figure 2D:
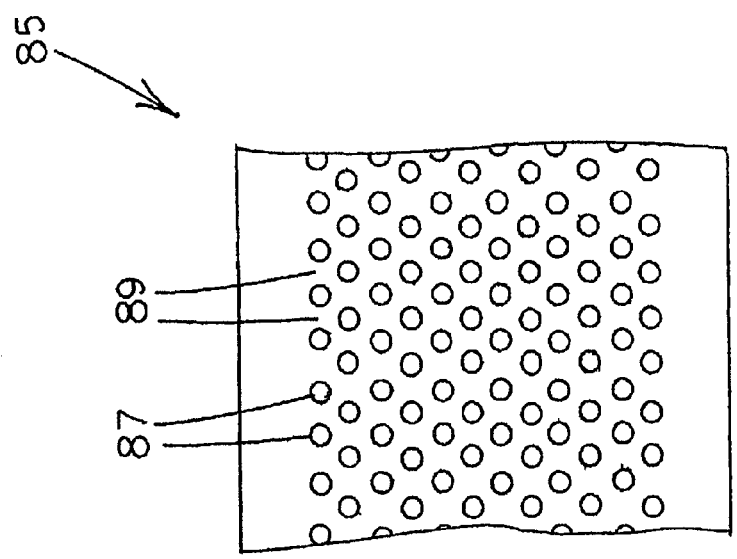
FIG. 2D is a plan view of a section of a contact region in accordance with another embodiment of the present disclosure.
Figure 2C:
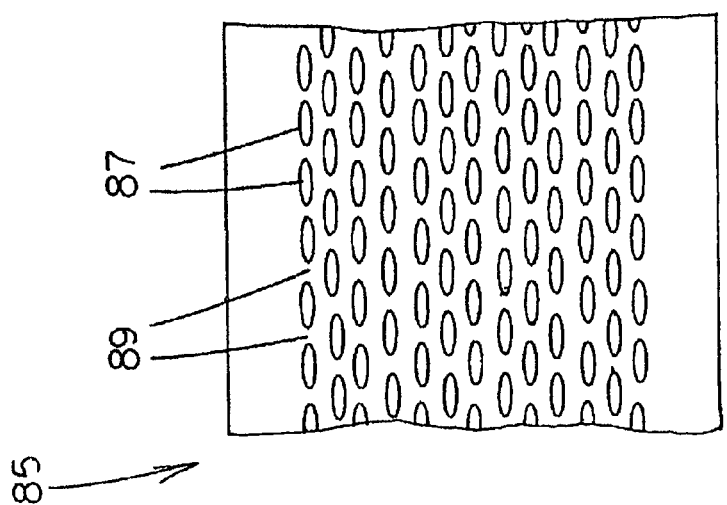
FIG. 2C is a plan view of a section of a contact region provided with the fastener receiving member in accordance with one embodiment of the present disclosure.

It will be further noted that in the embodiment illustrated in FIGS. 2A and 2B, each protrusion 87 has a generally rectilinear cross-section. The present disclosure, however, encompasses within its scope any cross-section suitable for realizing the tappable property of contact region 85. Hence, as another example, FIG. 2C illustrates an area of contact region 85 in which protrusions 87 are generally elliptical in cross-section. As a further example, FIG. 2D illustrates an area of contact region in which protrusions 87 are generally circular in cross-section. In addition, depending on the density and size of protrusions 87 and the pattern defined by the matrix, protrusions 87 may or may not be deformable as necessary to realize the tappable property of contact region 85.

As seen from the perspective of FIG. 2B, the resultant profile of contact region 85 is illustrated in one embodiment as being rounded to accommodate the rounded profile of head section 40 of fastener 10. The term "resultant" is meant to denote that the profile can be defined by the inside surface 81 itself with each protrusion 87 having a substantially uniform length, or alternatively, the profile can be defined by protrusions 87 of varying lengths. The present disclosure, however, is not limited to any specific profile for contact region 85. In addition, in some embodiments of the present disclosure, contact region 85 is not formed over the entire axial length of inside surface 81. Thus, in FIG. 2B, contact region 85 terminates at a lower section 95 of inside surface 81 (or substrate 91) proximate to second outer surface 64 of fastener receiving member 60.

While the profile of lower section 95 in FIG. 2A is cylindrical, other profiles for lower section 95 are suitable in accordance with the present disclosure. The respective profiles for contact region 85 and any exposed portion of inside surface 81 such as lower section 95 will be dictated in part by the shape of head section 40 of fastener 10, and also by the need to affix fastener 10 over a wide range of available insertion angles IA in relation to receiving member 60 and/or the bone material B or other object in which fastener 10 is to be anchored. Thus, in FIG. 4, a fastener 10 with a conical head section 40 is employed in connection with a receiving member 60 having a contact region 85 of cylindrical profile and a lower section 95 that tapers from second outer surface 64 to contact region 85. As another example, in FIG. 5, a fastener 10 with a rounded head section 40 is employed in connection with a receiving member 60 having a contact region 85 of converging/diverging or trumpet-shaped profile and a lower section 95 of tapering profile. It will be noted for all embodiments that the minimum inside diameter of contact region 85 should be large enough to provide clearance for elongate section 20 and its first thread 31 to pass through aperture A. As one example, the minimum inside diameter can range from approximately 0.5 to approximately 10 mm. In non-orthopaedic applications, the minimum inside diameter can be greater than 10 mm.

Figure 6:
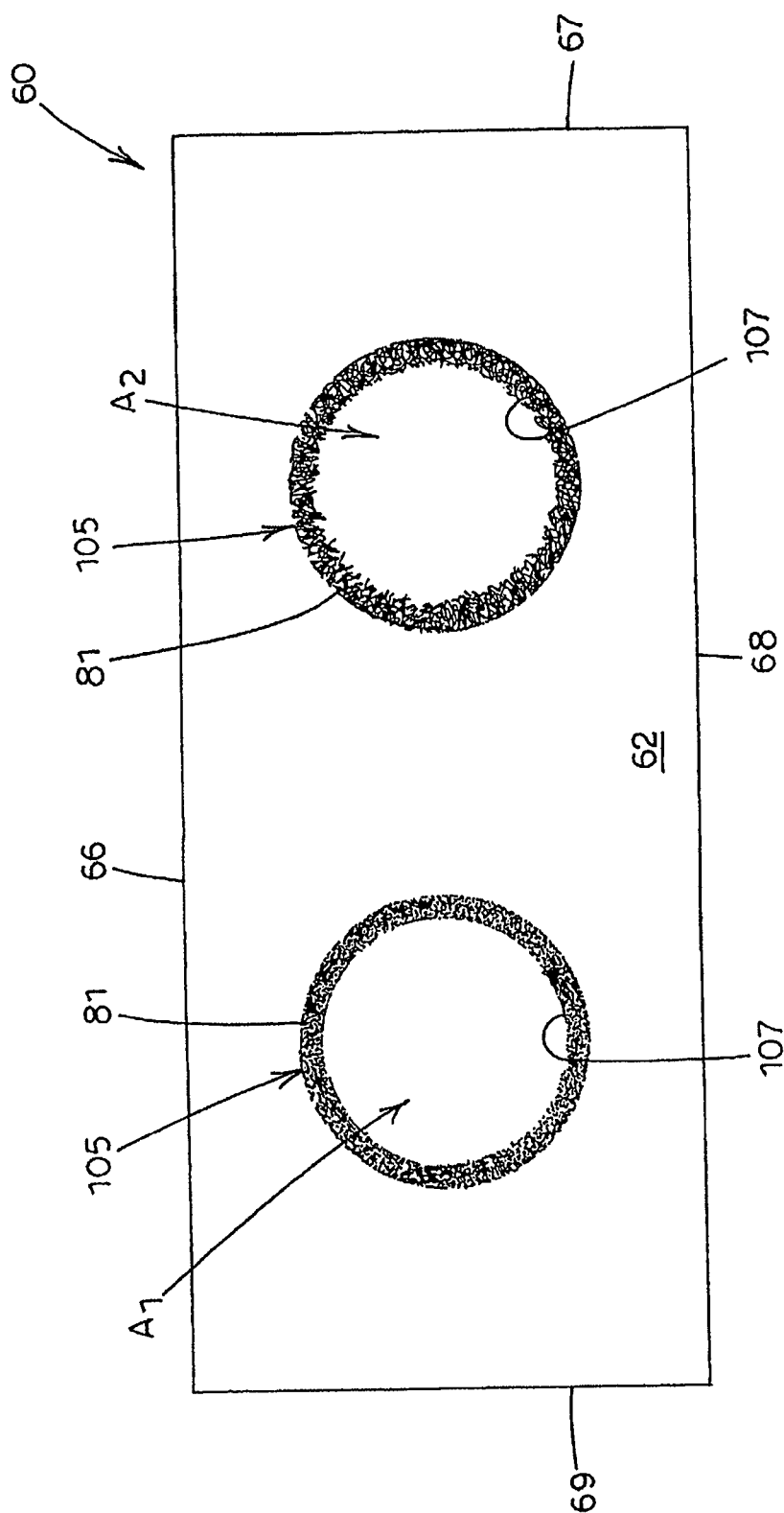
FIG. 6 is a top plan view of a fastener receiving member provided with an alternative contact region provided in accordance with the present disclosure.
Figure 7:
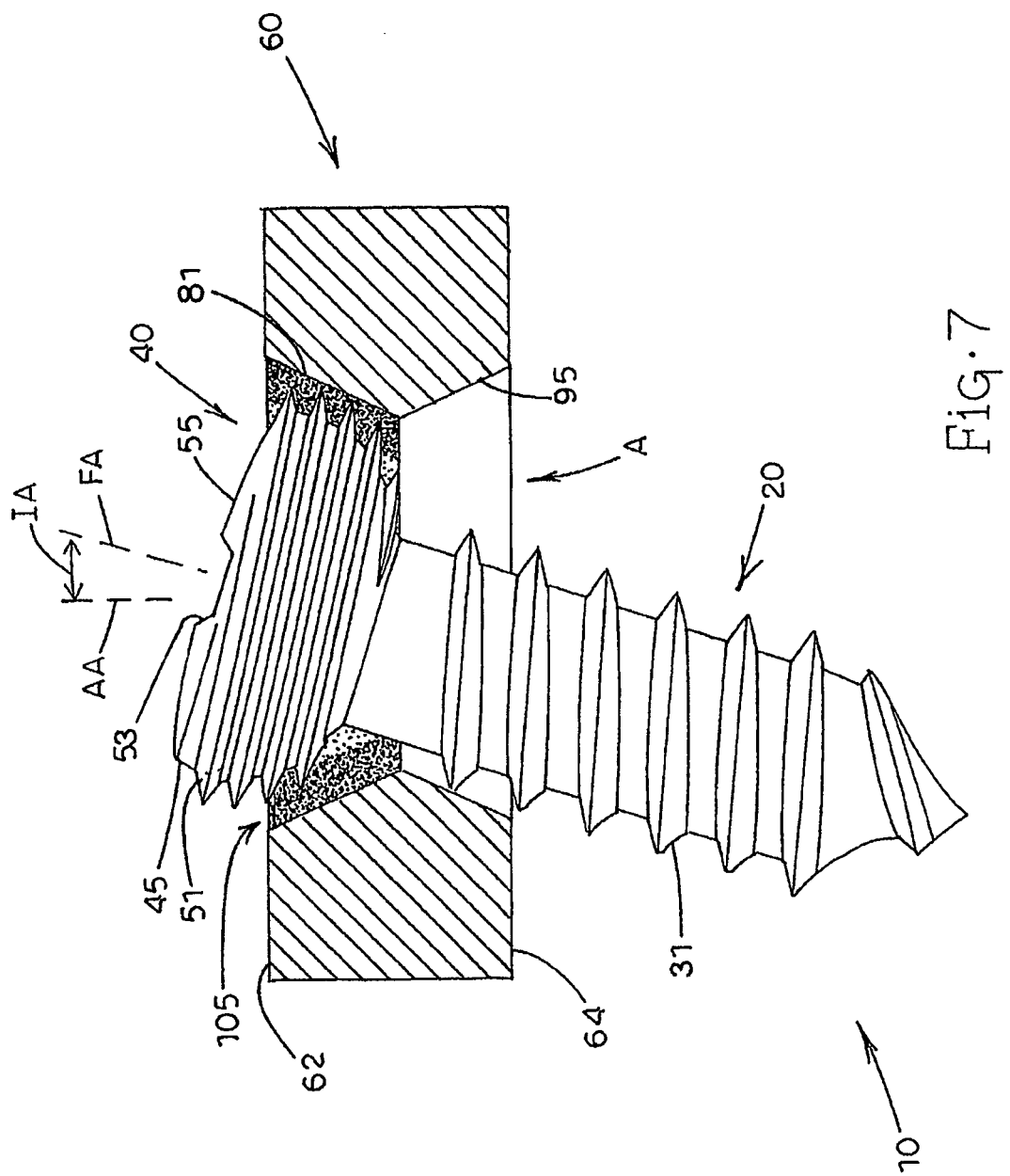
FIG. 7 is a partially cut away and vertical cross-sectional view illustrating the fastener affixed to the fastener receiving member illustrated in FIG. 6.

Referring now to FIGS. 6 and 7, an alternative embodiment of a tappable contact region, generally designated 105, is illustrated. In this embodiment, tappable contact region 105 takes the form of a matrix or mesh of fiber metal 107 that lines inside surface 81 of each aperture A of fastener receiving member 60. As understood by persons skilled in the art, fiber metal consists of a porous or interstitial aggregate of metal or metal alloy wires or fibers. The characteristic cross-sectional dimension of each fiber (e.g., diameter, width, or the like) can range from approximately 1 micron to approximately 25 mm. The porosity of the matrix can range from approximately 40 to approximately 90%. The fibers are often interlocked and kinked in any number of different patterns, and often has the appearance of steel wool. The aggregate can be formed by a variety of techniques. As one example, the fibers can be molded and sintered so as create metallurgical bonds between the fibers and a base surface. The composition of the fibers of contact region 105 can be any biocompatible material that provides contact region 105 with mechanical strength and deformability suitable for being tapped by fastener 10 in accordance with the present disclosure. Non-limiting examples include stainless steel, titanium, cobalt, chromium, tungsten, tantalum, molybdenum, gold, and alloys thereof.

An example of a method for affixing fastener 10 to fastener receiving member 60 will now be described by referring back to FIG. 3, with the understanding that the method can likewise be described in association with the other embodiments illustrated in FIGS. 4-7. It will be further understood that while the present example is given in the context of an orthopaedic surgical procedure, the present disclosure is not so limited. That is, the fastener/receiver system provided by the present disclosure can be applied to any procedure, surgical or non-surgical, in which a threaded fastener is to be tapped into an object and which would benefit by the ability to rigidly orient such fastener at a desired angle in relation to a mounting structure such as fastener receiving member 60.

Turning now to FIG. 3, the surgeon accesses the surgical site of interest, which can be, for example, an internal site at which a bone fracture F is located and requires stabilization to ensure proper healing. The surgeon mounts fastener receiving member 60 against bone material B at a desired location thereof in relation to the bone fracture F. A suitable alignment or mounting tool (not shown) can be employed to retain receiving member 60 in the desired position prior to complete affixation of fastener 10. The surgeon then selects an insertion angle IA, defined hereinabove, as the direction along which fastener 10 is to be inserted through a selected aperture A of receiving member 60 and subsequently driven into a target section of bone material B. If receiving member 60 includes more than one aperture A, the surgeon also selects the specific aperture A to be used. After selecting insertion angle IA and aperture A, the surgeon inserts elongate section 20 of fastener 10 through aperture A until the tip of elongate section 20 contacts bone material B beneath aperture A. In some cases, at this point a hole might be drilled or tapped into bone material B along insertion angle IA to facilitate the initial tapping by fastener 10. The surgeon then inserts an appropriate driving tool (not shown) into recess 53 of head section 40 of fastener 10, and manipulates the driving tool to rotate fastener 10 while forcefully bearing fastener 10 against bone material B. This causes first thread 31 of elongate section 20 to tap into bone material B and anchor fastener 10 to bone material B. As elongate section 20 is driven further through aperture A and into bone material B, head section 40 eventually encounters contact region 85 of aperture A. Due to the intervening presence of contact region 85, the continued driving of fastener 10 into bone material B at this stage causes second thread 51 of head section 40 to tap into contact region 85, thereby rigidly affixing fastener 10 to receiving member 60 at the desired insertion angle IA.

The manner by which head section 40 of fastener 10 is affixed to aperture A of receiving member 60 depends on whether contact region 85 illustrated in FIGS. 2A-3 or contact region 105 illustrated in FIGS. 6 and 7 is provided. In the use of contact region 85, second thread 51 of head section 40 is driven through a series of available interstices 89 (see, e.g., FIGS. 2C and 2D) and between a series of protrusions 87 adjacent to these interstices 89. The driving of second thread 51 causes this series of protrusions 87 to contact second thread 51 and maintain fastener 10 at the desired insertion angle IA. As described hereinabove, protrusions 87 contacting second thread 51 may or may not deform or otherwise move in response to the driving of second thread 51 into contact region 85. On the other hand, in the use of contact region 105, the metal fibers will deflect in response to the driving of second thread 51 and envelop second thread 51. The mechanical strength of the fibers contacting or proximate to second thread 51 is sufficient to maintain fastener 10 at the desired insertion angle IA. Some of the fibers may be cut in response to the driving of second thread 51 into contact region 105. With the use of either contact region 85 or contact region 105, the driving of second thread 51 through aperture A in effect forms a custom internal thread in contact region 85 or 105 that is complimentary to the orientation and structure of second thread 51 and turns in relation to fastener axis FA.

Depending on the nature of the procedure being executed, the surgeon can affix additional fasteners 10 to additional apertures A of receiving member 60, either at the same insertion angle IA as the illustrated fastener 10 or at different angles. It will be noted that, depending on the number of fasteners 10 utilized and how far each is threaded into its corresponding aperture A, the mechanical strength of the interface between each corresponding second thread 51 and contact region 85 or 105 can be made sufficient to cause compression of receiving member 60 against bone material B if desired by the surgeon.

As an alternative to the embodiments specifically illustrated in FIGS. 1-7, the interface between second thread 51 of head section 40 and contact region 85 or 105 of aperture A could be reversed. That is, head section 40 of fastener 10 could be provided with contact region 85 or 105, and aperture A of fastener receiving member 60 could be provided with second thread 51. This alternative embodiment likewise enables fastener 10 to be rigidly secured non-coaxially to aperture A.

Anti-Unscrewing Embodiments of Multi-Angular Bone Screw/Plate Systems

I. Anti-Unscrewing System

Figure 8:
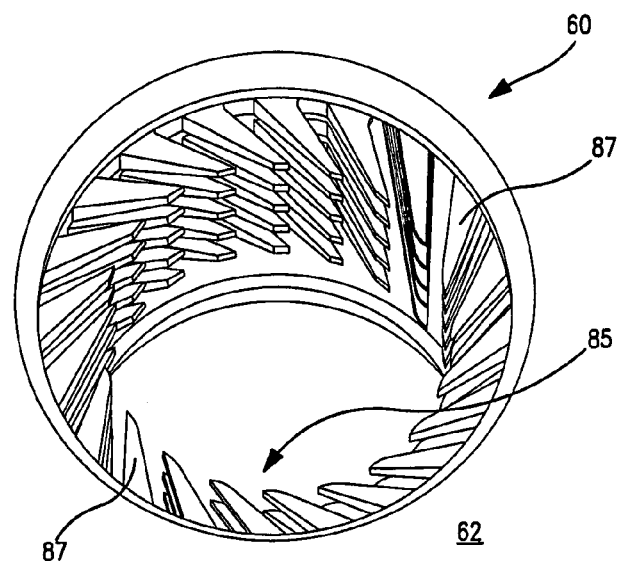
FIG. 8 is a top perspective view of a section of a fastener receiving member provided in accordance with the present disclosure.

Other aspects can be provided in accordance with the present disclosure that prevent fastener 10 from backing out of fastener receiving member 60, as shown in FIG. 8. Such prevention is desirable to avoid fastener 10 from becoming loose and thereby failing to maintain fastener receiving member 60 in a secure and fixed position. Furthermore, in anatomically critical areas, such as the anterior cervical spine, impingement of backed-out fastener 10 on overlying structures can create the risk of significant morbidity and mortality. Thus, an anti-unscrewing system is desirable to prevent unscrewing or backing out of fastener 10 from plate or fastener receiving member 60.

Figure 9:
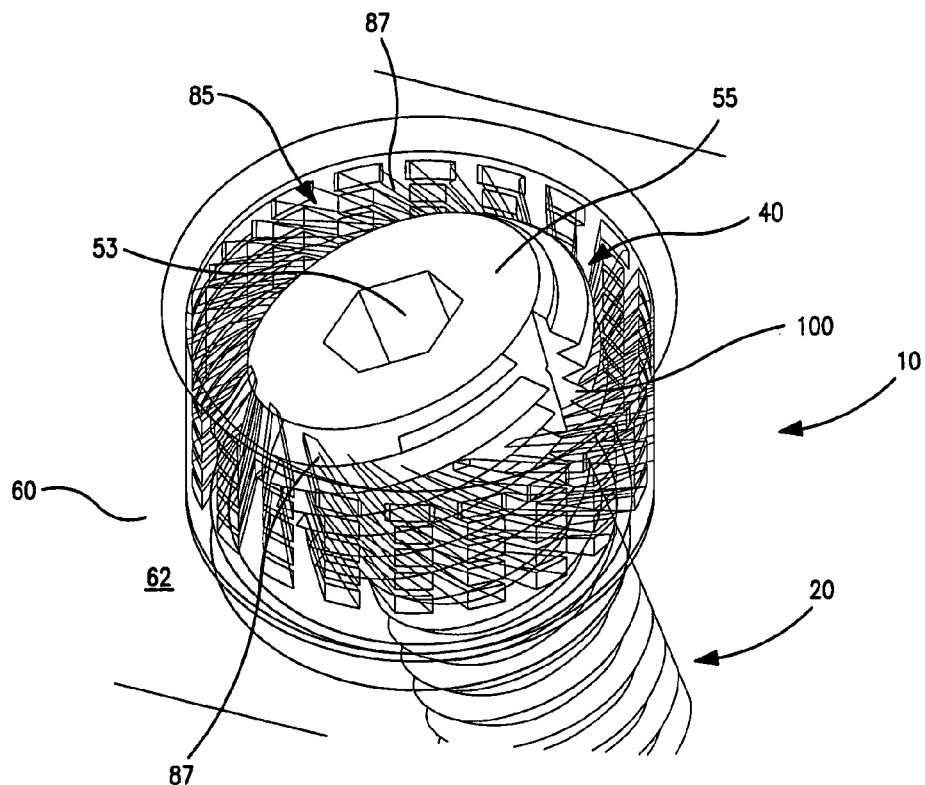
FIG. 9 is a top perspective view of a section of a fastener receiving member provided in accordance with the present disclosure in which the fastener comprises at least one slot for providing anti-unscrewing properties.
Figure 10:
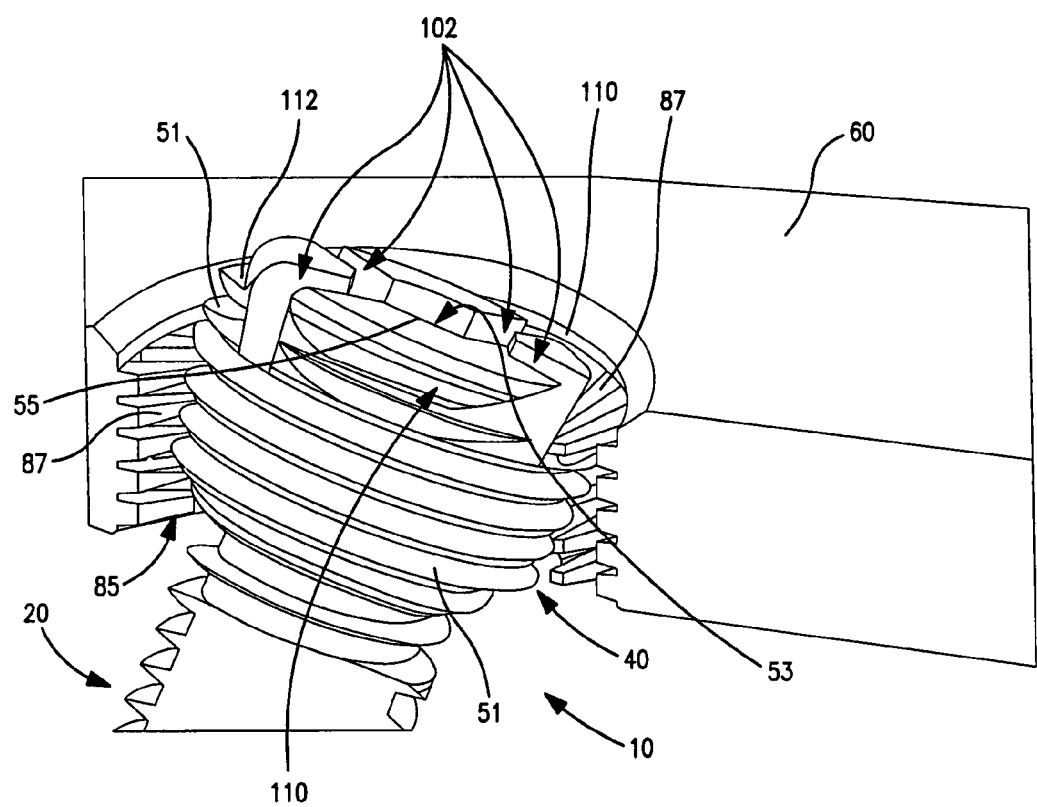
FIG. 10 is a partially cut away and vertical cross-sectional view illustrating a fastener having a plurality of fastener slots being positioned in the fastener receiving member provided in accordance with the present disclosure.

In one aspect for providing an anti-unscrewing function, as illustrated in FIG. 9, fastener 10 can include an at least one slot generally designated 100 that can be filled with protrusions 87 of contact region 85 of fastener receiving member 60 upon insertion of fastener 10 into contact region 85 of fastener receiving member 60, thereby preventing fastener 10 from unscrewing or backing out and serving to lock fastener 10 in a permanent manner. In other aspects of the present disclosure, as depicted in FIG. 10, fastener 10 can include a plurality of slots generally designated 102 such that protrusions 87 fill multiple slots 102 of fastener 10.

Figure 11:
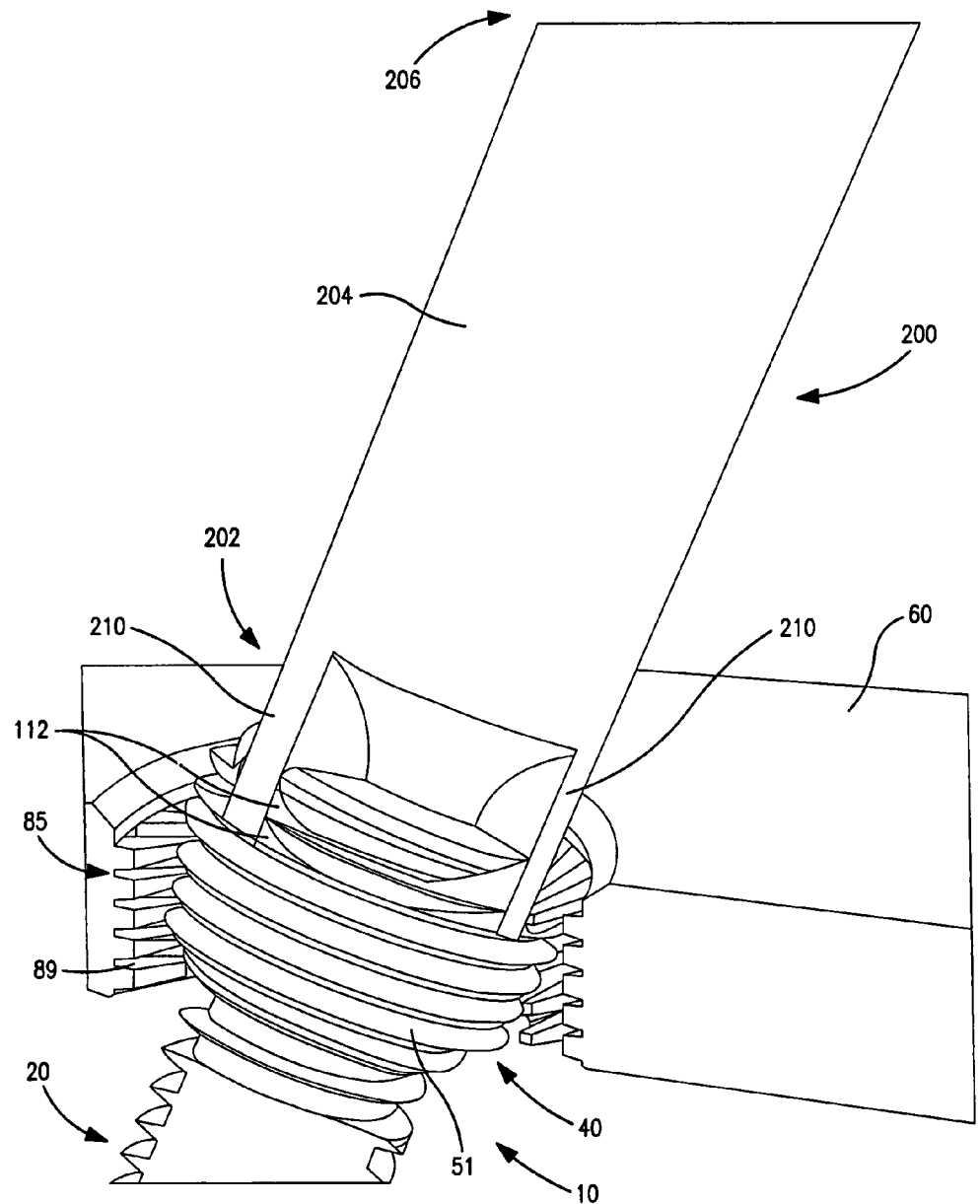
FIG. 11 is a partially cut away and vertical cross-sectional view of a bone screw/plate system for providing anti-unscrewing properties provided in accordance with the present disclosure.

In certain instances, though, removal of fastener 10 from the anti-unscrewing system as disclosed herein may be desirable or necessary. Thus, as shown in FIG. 11, a fastener driver generally designated 200 can be provided for inserting and removing fastener 10 from fastener receiving member 60 of the anti-unscrewing system. Fastener driver 200 can serve to deflect protrusions 87 out of the at least one slot 100 or plurality of slots 102 to facilitate insertion or removal of fastener 10 from contact region 85 of fastener receiving member 60.

Also, an angular driver tool generally designated 300 having an end portion designated 310 can be provided for improving angular adjustability and control of the insertion orientation of fastener 10. By providing tool 300 with a nipple 320 (FIGS. 13 and 14) integral therewith or a rod 340 (FIGS. 15 and 16) having a threaded end 342 that can extend within a cavity generally designated 48 (FIG. 12) of fastener 10, a surgeon can more precisely control the angle of insertion of fastener 10, while ensuring that fastener 10 will not separate from angular driver tool 300. In other words, fastener 10 will not fall off end portion 310 of tool 300 when the surgeon tilts tool 300 to insert fastener 10 at an angular orientation. In other aspects, the features of fastener driver 200 and angular driver tool 300 can be combined such that the combination provides improved angular insertion control of fastener 10 while also effectuating insertion and removal of a fastener used in an anti-unscrewing system as provided.

A. Anti-Unscrewing Fastener

With reference to FIG. 9, head section 40 of fastener 10 can include at least one slot 100 about its outer circumference that can extend from top surface 55 downward. Slot 100 can provide anti-unscrewing properties to prevent backing out of fastener 10 from fastener receiving member 60. Furthermore, slot 100 can extend downward the entire length of head section 40 or terminate lengthwise at any finite point along head section 40. Slot 100 can be of any width and depth. Protrusions 87 of fastener receiving member 60 can be angled such that protrusions 87 permit fastener 10 to rotate in one direction, but resist rotation in the opposite direction. To facilitate the turning of fastener 10 by the user thereof, head section 40 can include recess 53 for the insertion of an appropriate tool such as a screwdriver, key, or wrench. The shape of recess 53 can be a single or cross-shaped slot, a square, a hexagon, a star, or the like.

To prevent removal and backing out of fastener 10 protrusions 87 project into slot 100 such that fastener 10 will catch on and be engaged by protrusions 87 to prohibit reverse rotation or backing out of fastener 10. Attempting to remove fastener 10 in such embodiments requires a strong torsional force that can break protrusions 87, thereby littering the surgical field therewith, or that can bend protrusions 87 such that they would no longer function. Therefore, it would also be advantageous to have an instrument, such as fastener driver 200 discussed further below, that facilitates removal of fastener 10 having slot 100 from fastener receiving member 60.

In other aspects, such as shown in FIG. 10, head section 40 can include a plurality of spaced-apart slots 102. Slots 102 can provide anti-unscrewing properties to prevent backing out of fastener 10. Slots 102 can extend from top surface 55 of head section 40 of fastener 10 and downward and terminate at any length along head section 40. Slots 102 can also perform the same function as slot 100 in that protrusions 87 can project thereinto for effectuating non-rotational movement of fastener 10 in a reverse manner. Slots 102 can also extend radially inwardly within head section 40 to facilitate engagement of a screwdriver type tool for rotating fastener 10, thereby also forming a plurality of arcuate portions therebetween that are generally designated 110. Arcuate portions 110 can each also include an extension of second thread 51 thereon, which second thread 51 generally extends around the head of fastener 10. Second thread 51 can have a beveled portion generally designated 112 proximate to slots 102 to prevent second thread 51 from catching on protrusions 87. Slots 102 can be of any number, shape, and design. Also, slots 102 can terminate or transition into recess 53 of head section 40 for the insertion of an appropriate tool having a corresponding shape.

Figure 12:
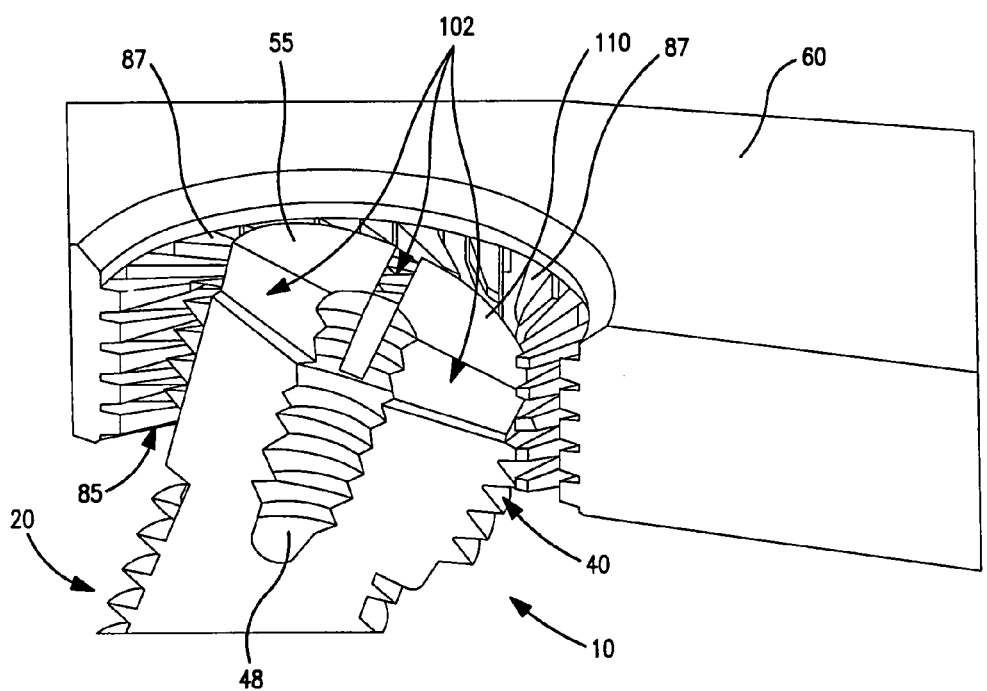
FIG. 12 is a partially cut away and vertical cross-sectional view of a fastener receiving member having a fastener positioned therein wherein the fastener has a cavity that can provide improved angular control of the fastener in accordance with the present disclosure.

In other aspects, rigid angular control of fastener 10 can be achieved by providing cavity 48 within fastener 10, as depicted in FIG. 12. Cavity 48 can be substantially elongate and can be configured to receive a screwdriver type instrument, for example, tool 300 as discussed further below. Cavity 48 can be threaded to matingly receive a threaded portion of tool 300, thereby allowing fastener 10 to be angled without risk of fastener 10 separating from and falling off of tool 300. Furthermore, cavity 48 can extend to any depth within fastener 48 and can be of any suitable shape and size. Also, cavity 48 can extend entirely through fastener 10 such that fastener 10 is cannulated for receiving a guide wire 400 and the like.

B. Anti-Unscrewing Driver

An instrument can be configured for use in inserting and removing fastener 10 from an anti-unscrewing system such as that in the present disclosure. Fastener driver 200 can be used to insert fastener 10 into fastener receiving member 60 to provide anti-unscrewing properties when fastener 10 includes slot 100 or slots 102. As shown in FIG. 11, fastener driver 200 can be substantially elongate.

In one aspect, driver 200 can include a fastener receiving end generally designated 202, an elongate shaft 204, and an operational end generally designated 206. Fastener receiving end 102 can include a plurality of slot engagement portions 210 that are sized so as to be fittingly received within slots 102 of head section 40 of fastener 10, such that rotational torque can be provided when fastener receiving end 202 is rotated. Furthermore, slot engagement portions 210 can prevent protrusions 87 from projecting into slots 102 during rotational advancement of fastener 10 by filling slots 102, thereby allowing fastener 10 to rotate within fastener receiving member 60 without protrusions 87 impeding rotation by catching in slots 102. Upon removal of driver 200, protrusions 87 can engage fastener 10 within slots 102 in an anti-unscrewing manner.

To remove fastener 10, slot engagement portions 210 of driver 200 can be inserted into slots 102, thereby deflecting protrusions 87 radially outwardly and out of slots 102. When protrusions 87 are no longer within slots 102 and impeding rotation, fastener 10 can be advanced outwardly from fastener receiving member 60 for removal of fastener 10 therefrom. As stated above, second thread 51 can have a beveled portion 112 to prevent protrusions 87 from catching thereon.

C. Angular Insertion Tool

Figure 14:
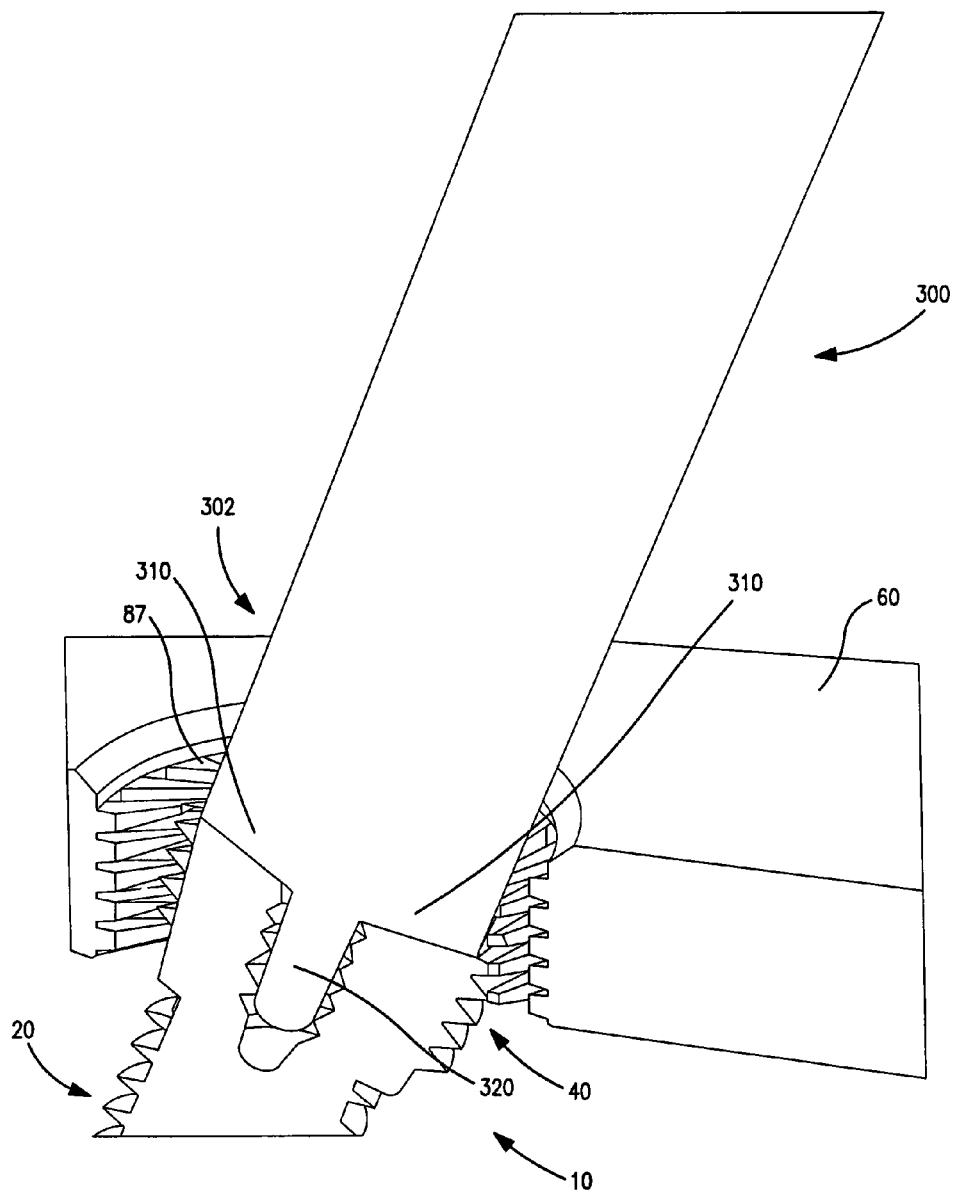
FIG. 14 is a vertical cross-sectional view illustrating the bone screw/plate system of FIG. 13 in which the fastener driver is shown in cross-section.
Figure 15:
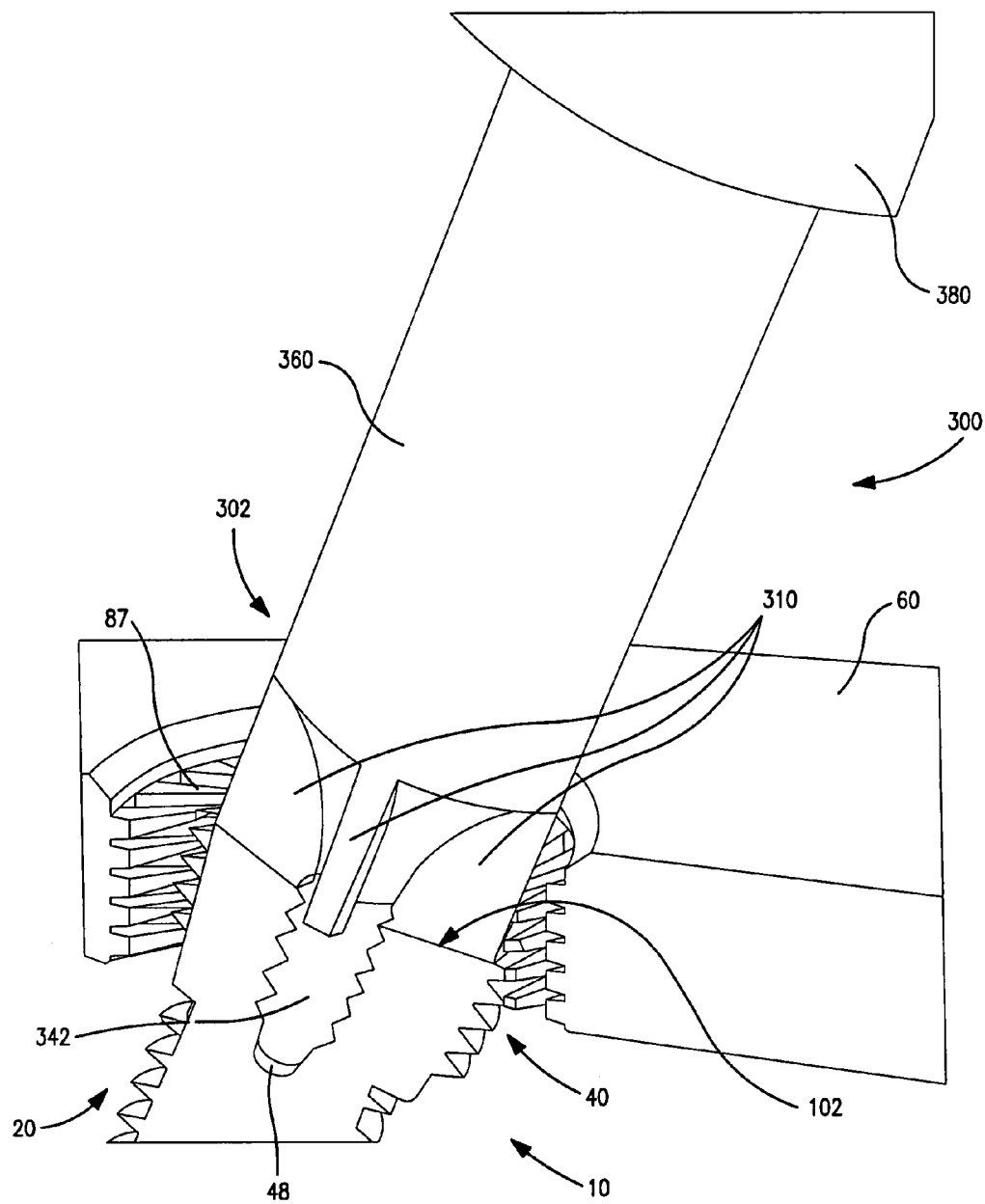
FIG. 15 is a partially cut away and vertical cross-sectional view illustrating another bone screw/plate system for providing anti-unscrewing properties and improved angular insertion control of a fastener in accordance with the present disclosure.
Figure 16:
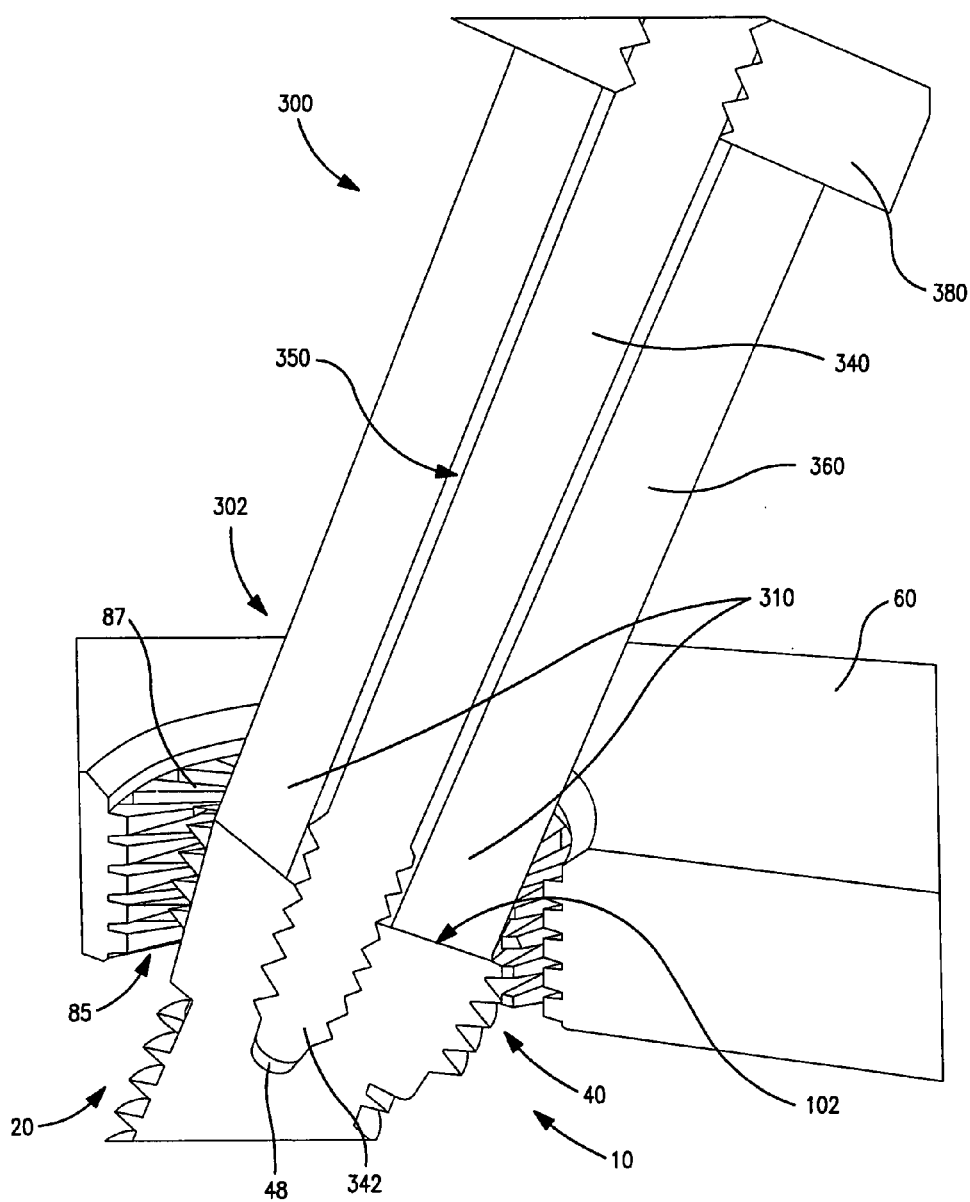
FIG. 16 is a vertical cross-sectional view illustrating the system of FIG. 15 in which the fastener driver is shown in cross-section.

Angular insertion of fastener 10 is often needed, including during use in the disclosed anti-unscrewing system. Angular driver tool 300 can be configured to provide improved rigid angular control of fastener 10 during angular insertion, as illustrated in FIGS. 14-16. Preventing fastener 10 from falling off tool 300 can be extremely important to the surgeon when attempting to insert fastener 10 at an angle. In one embodiment, slot engagement portions 310 can be substantially deep to prevent fastener 10 from slipping off of tool 300, and thus fastener receiving end 302 can lock angular direction in an improved manner.

Figure 13:
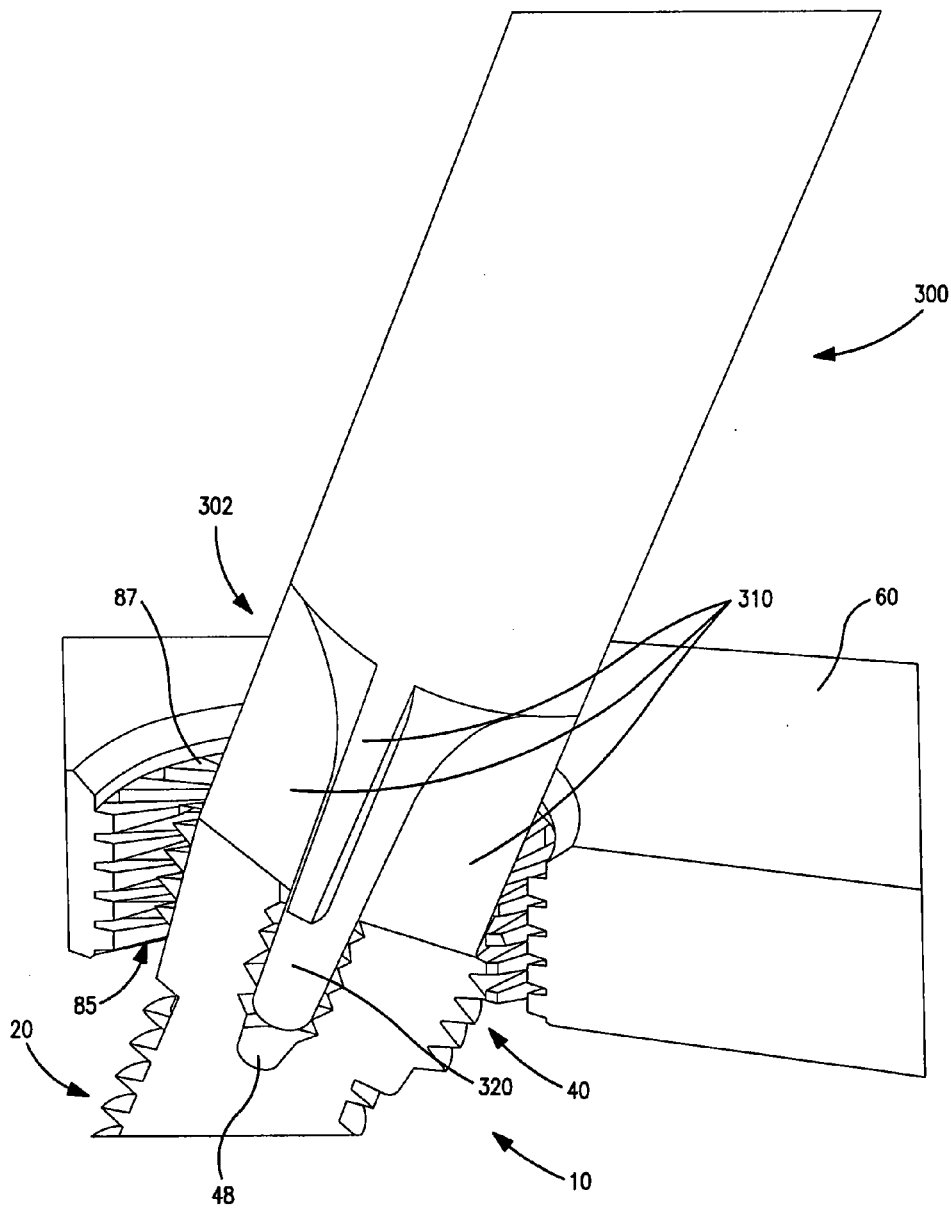
FIG. 13 is a partially cut away and vertical cross-sectional view illustrating a bone screw/plate system for providing anti-unscrewing properties and improved angular insertion control of a fastener in accordance with the present disclosure.

In other aspects, such as those illustrated in FIGS. 13 and 14, tool 300 can further include a nipple 320 that can be matingly received within cavity 48 of fastener 10. Insertion of nipple 320 within cavity 48 gives better control of fastener 10 than do simple cross head screwdrivers, from which fasteners can easily fall off, that are commonly used in surgical applications. Nipple 320 can be inserted into cavity 48 while slot engagement portions 310 are received within slots 102. Thus, the surgeon can angle tool 300 and fastener 10 without worry that fastener 10 will fall off end 302, thereby providing improved angular control to ensure that the correct insertion angle of fastener 10 is achieved. Nipple 320 can be threaded or not be threaded. Cavity 48 can be threaded or not be threaded. Furthermore, nipple 320 can assist the surgeon in holding tool 300 perfectly coaxial with fastener 10 to eliminate the possibility that tool 300 is not coaxial and that slots 102 are not filled by slot engagement portions 310, making fastener 10 difficult to unscrew due to protrusions 87 projecting into slots 102 in locked manner.

In yet another aspect, as shown in FIGS. 15 and 16, tool 300 can be configured to provide absolute rigid angular control of fastener 10 when the surgeon cannot afford for fastener 10 to separate from tool 300, such as during spinal applications. In such embodiments, tool 300 can include a driver rod 340 that can have a threaded end 342 for matingly engaging cavity 48. Cavity 48 can also be threaded to matingly receive threaded end 342. Tool 300 can include a sleeve portion 360 that can define a cannulated shaft generally designated 350 (FIG. 16) for receiving driver rod 340. Cannulated shaft 350 can extend entirely through tool 300. Driver rod 340 can have a ram 380 on the end opposite threaded end 342.

In use, driver rod 340 can be rotated into head section 40 of fastener 10 at cavity 48. Then, sleeve portion 360 can slide down over driver rod 340 such that slot engagement portions 310 of tool 300 fit into slots 102 in head section 40 of fastener 10, thereby providing torsional attachment such that fastener 10 can be turned during the action of driving fastener 10 into bone and into contact region 85 of fastener receiving member 60 and filling slots 102 such that protrusions 87 can no longer catch or project within slots 102 (which allows fastener 10 to be unscrewed when removal is required). Then, ram 380 can be threaded onto driver rod 340 so that when ram 380 is screwed forward it rams sleeve portion 360 down onto fastener 10, which is maintained in a fixed position because it is already fastened to driver rod 340. That is, fastener 10 can fasten onto driver rod 340, sleeve portion 360 can then slide down to give torsional control and fill slots 102, and then sleeve portion 360 can be held firmly in that position by ram 380.

Once fastener 10 is fastened into bone and contact region 85, ram 380 can be backed off, allowing sleeve portion 360 to be pulled back. As a result, protrusions 87 can drop into slots 102 so that fastener 10 will not back-out of fastener receiving member 60, thereby allowing the surgeon to unscrew driver rod 340 from fastener 10 without unscrewing fastener 10. When removal of fastener 10 is necessary, for example after healing, the surgeon can clean out soft tissue from within slots 102 of fastener 10, then screw in driver rod 340, then insert sleeve portion 360 to fill slots 102 and deflect protrusions 87, then lock tool 300 into place with ram 380, and then unscrew the entire assembly. Once ram 380, driver rod 340 and sleeve portion 360 are all assembled to fastener 10, they all can be configured to cooperatively function to rotate fastener 10 in an angular direction (i.e., they rotate together and act as one assembly).

Figure 17:
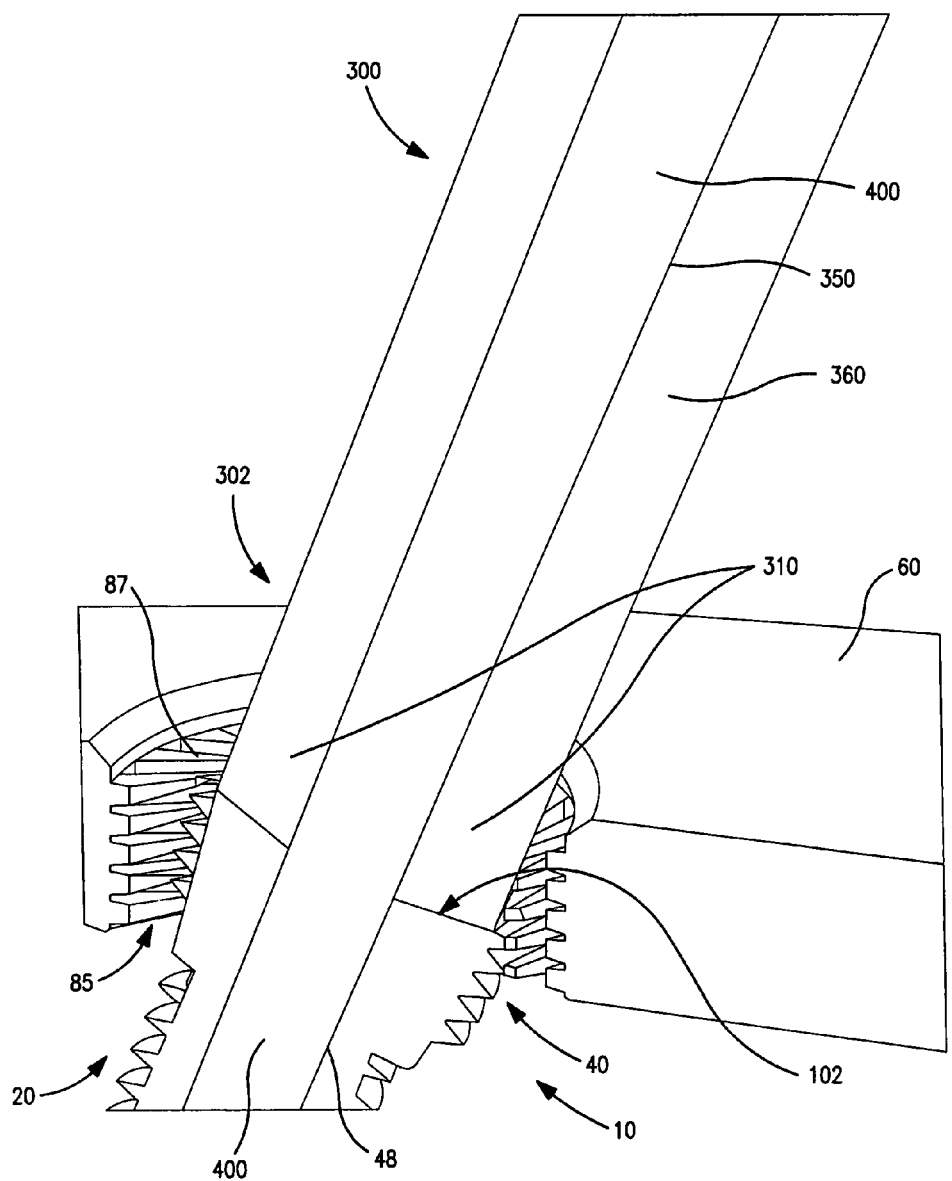
FIG. 17 is a partially cut away and vertical cross-sectional view illustrating an anti-unscrewing bone screw/plate system in use with a guide wire to control angular insertion of the fastener in accordance with the present disclosure.

In another aspect, as shown in FIG. 17, fastener 10 can be cannulated such that cavity 48 runs the entire length of fastener 10 and guide wire 400 can pass entirely through fastener 10 in a substantially coaxial manner. Tool 300 can include sleeve 360 that defines cannulated shaft 350 such that guide wire 400 can pass entirely therethrough in a substantially coaxial manner. Tool 300 can further include slot engagement portions 310 such that tool 300 can be used with the anti-unscrewing system as disclosed, while also providing improved angular insertion control. In use, the surgeon can first run guide wire 400 through contact region 85 having protrusions 87 into a predetermined location in bone that fastener 10 will enter, which can be confirmed with x-ray imaging. The surgeon can slide the cannulated fastener 10 over guide wire 400 and then slide tool 300 over guide wire 400, wherein tool 300 can then drive fastener 10. Guide wire 400 can provide the necessary alignment of all the elements rather than using nipple 320 or driver rod 340 to ensure fastener 10 remains on end portion 302 of tool 300 in the correct angular orientation.

D. Anti-Unscrewing and Angular Insertion Instrument

In other aspects, elements of fastener driver 200 and angular driver tool 300 can be combined such that the combination can produce instruments, as illustrated in FIGS. 13-17, having slot engagement portions 210, 310 to facilitate use with an anti-unscrewing system and that further provide rigid angular insertion control. In such embodiments, slot engagement portions 210, 310 can be coupled with nipple 320 or threaded end 342 of driver rod 340 to exhibit both anti-unscrewing and angular insertion properties.

Plate Puller Device and Systems for Use Therewith

Figure 18:
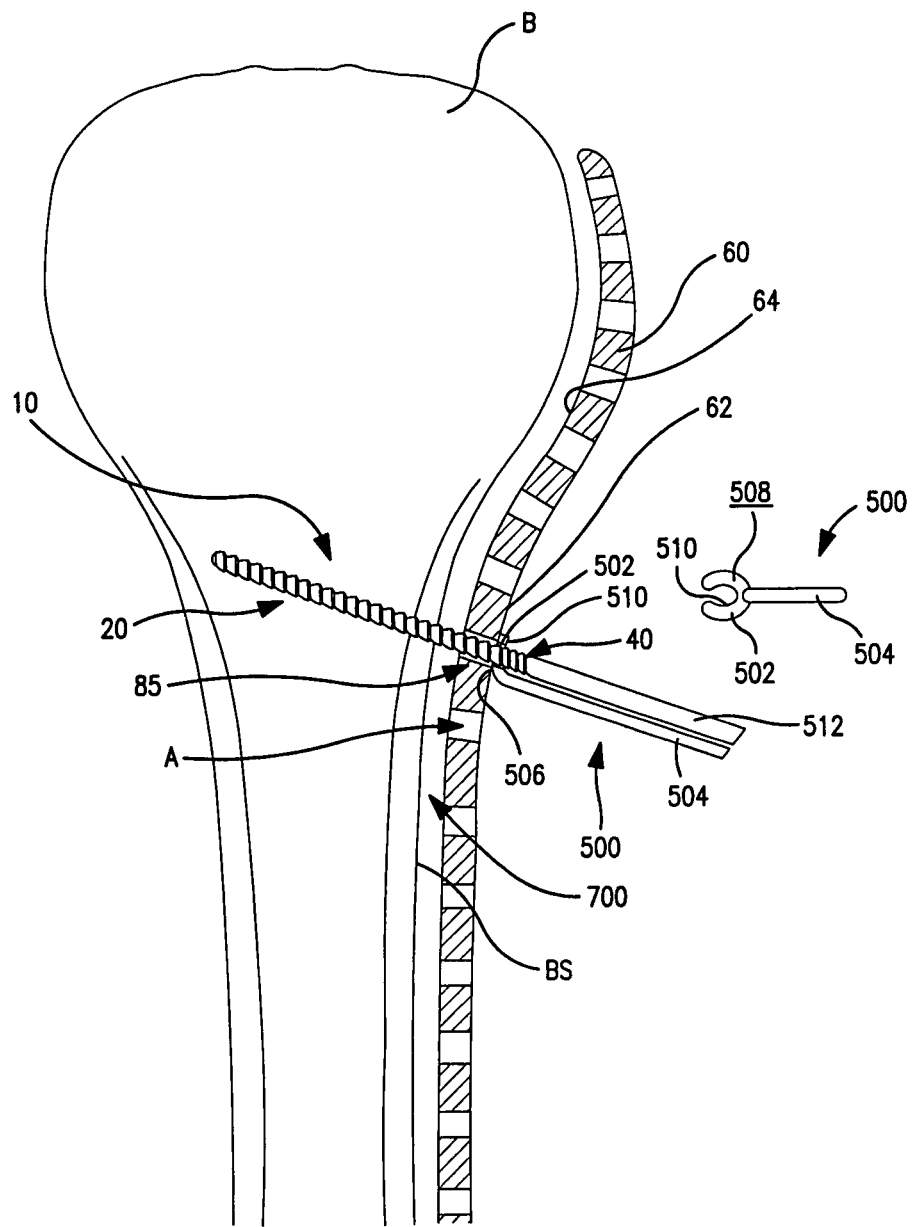
FIG. 18 is a vertical partial cross-sectional view illustrating a first plate puller device in use in accordance with the present disclosure.
Figure 19:
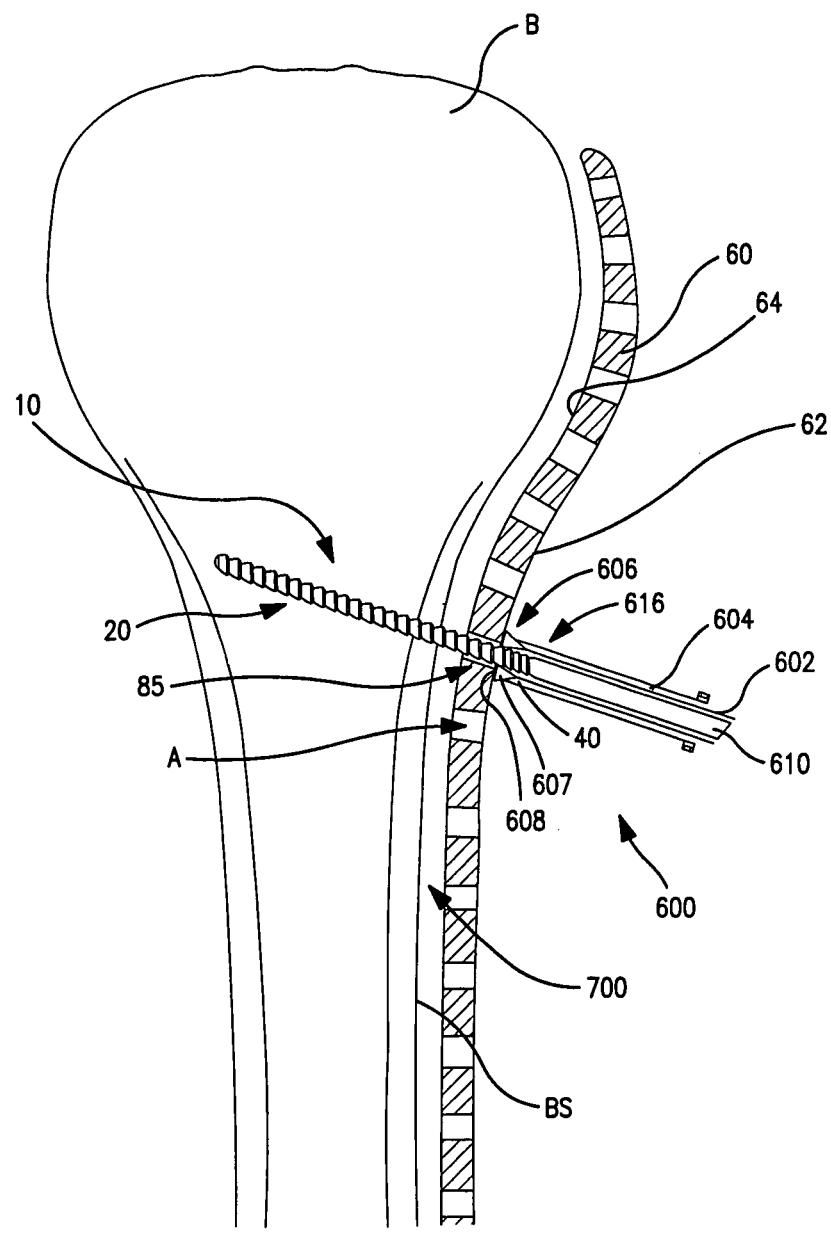
FIG. 19 is a vertical partial cross-sectional view illustrating a second plate puller device having a grasper portion and grasper sleeve in accordance with the present disclosure.

Other aspects can be provided in accordance with the present disclosure that prevent head section 40 of fastener 10 from advancing prematurely within contact region 85 of aperture A of fastener receiving member 60, as shown in FIGS. 18 and 19. Such prevention is desirable to avoid head section 40 of fastener 10 from becoming locked in contact region 85 before fastener receiving member 60 has been pulled completely against a bone surface BS of bone B such that fastener receiving member 60 and bone surface BS are in contact and abutment. Such contact and abutment are desirable for fastener receiving member 60 to provide the support and function desired at a bone fracture point. Permitting head section 40 to lock within fastener receiving member 60 before fastener receiving member 60 is abutting bone surface BS can lead to an undesirable "stand off" position in which there is a gap 700 therebetween, which cannot be corrected due to head section 40 of fastener 10 being locked within contact region 85 of fastener receiving member 60. Thus, it is desirable to have a device that can prevent fastener 10 from locking to fastener receiving member 60 until fastening receiving member 60 contacts bone surface BS. Such a device can not only be used with the fastener locking mechanism of the present disclosure that includes a fastener receiving member having a tappable contact region as described hereinabove, but the device can also be used with any other available fastener locking technology.

In one aspect, as shown in FIG. 18, a plate puller device 500 can be provided to prevent head section 40 of fastener 10 from entering aperture A of fastener receiving member 60. Plate puller device 500 can comprise a head portion 502 and an extension rod 504. Head portion 502 can be integral with extension rod 504. Head portion 502 can be generally U-shaped such that head portion 502 can slide around elongate section 20 of fastener 10. Head portion 502 can have a bottom surface 506 and a top surface 508. Bottom surface 506 can be flat to abut against first outer surface 62 of fastener receiving member 60. In other aspects, bottom surface 506 can be any shape configured to match the shape of first outer surface 62. Top surface 508 can have a beveled portion 510 for mating to the contour of head section 40 of fastener 10.

FIG. 18 illustrates a first plate puller device 500 in use with fastener 10 and fastener receiving member 60. A surgeon can position second outer surface 64 of fastener receiving member 60 against bone surface BS of bone B. Elongate section 20 of fastener 10 can be inserted through aperture A of fastener receiving member 60 without contacting contact region 85. Once elongate section 20 encounters bone surface BS, a screwdriver 512 or other suitable tool can be used to insert fastener 10 within bone B. Undesirably, gap 700 can form during the insertion of fastener 10 with screwdriver 512. Gap 700 can remain between second outer surface 64 of fastener receiving member 60 and bone surface BS when head section 40 of fastener 10 locks into contact region 85. Subsequent rotation of fastener 10 when head section 40 is locked in contact region 85 of fastener receiving member 60 does not close gap 700.

To that end, plate puller device 500 can be inserted between head section 40 of fastener 10 and first outer surface 62 of fastener receiving member 60. Head portion 502 of plate puller device 500 can be generally U-shaped so that head portion 502 can slide around elongate section 20 of fastener 10 after fastener 10 has been inserted into aperture A of fastener receiving member 60. The U-shape also allows the surgeon to remove plate puller device 500 after performing its function. The surgeon can grip extension rod 504 of plate puller device 500 to hold plate puller device 500 in position.

By positioning head portion 502 of plate puller device 500 between head section 40 of fastener 10 and first outer surface 62 of fastener receiving member 60, plate puller device 500 can prevent head section 40 of fastener 10 from advancing within aperture A and engaging contact region 85 of fastener receiving member 60. By preventing this advancement, elongate section 20 of fastener 10 continues to advance into bone B as the surgeon rotates fastener 10, thereby pulling fastener receiving member 60 against bone surface BS and closing gap 700. After closing gap 700, the surgeon can slide plate puller device 500 out from between head section 40 of fastener 10 and first outer surface 62 of fastener receiving member 60. Head section 40 of fastener 10 can now be advanced within aperture A of fastener receiving member 60 wherein head section 40 can engage contract region 85 in a locking manner.

Figure 20:
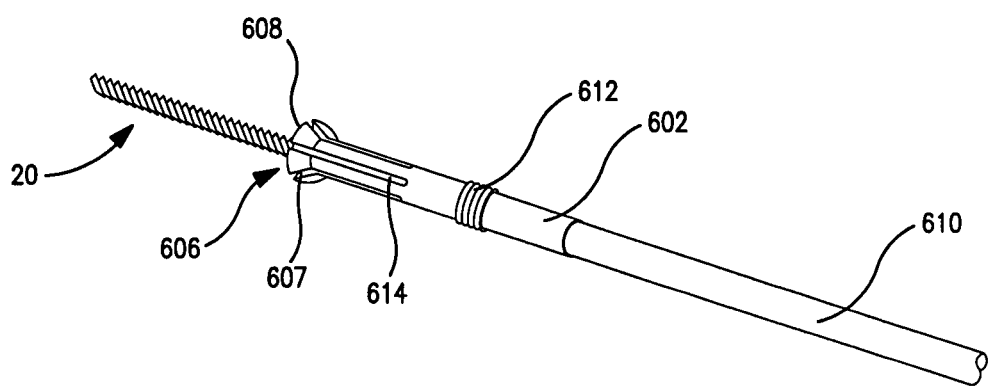
FIG. 20 is a perspective view illustrating the second plate puller device in accordance with the present disclosure with the grasper sleeve removed for clarity of illustration.
Figure 21:
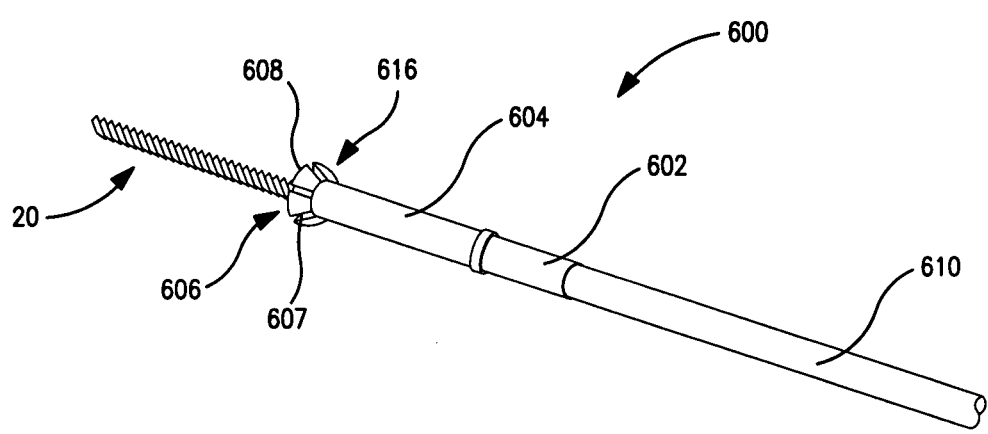
FIG. 21 is a perspective view illustrating the second plate puller device according to FIG. 19 and showing both the grasper portion and the grasper sleeve.

In another aspect, as shown in FIGS. 19-21, a second plate puller device 600 can comprise a grasper portion 602, a grasper sleeve 604 (not shown in FIG. 20) and a screwdriver 610. Grasper portion 602 can be positioned around screwdriver 610. Grasper portion 602 can be attached to screwdriver 610 in some manner or in other aspects grasper portion 602 can slide over the portion of screwdriver 610 that engages head section 40 of fastener 10. Grasper portion 602 can be generally elongate and can comprise a head portion 606. Head portion 606 of grasper portion 602 can be generally wedge shaped and can comprise a plurality of wedges 607. Head portion 606 of grasper portion can have a bottom surface 608 that can be generally flat to abut against first outer surface 62 of fastener receiving member 60. Grasper portion 602 can include a plurality of slits 614 (see FIG. 20) that can extend axially from bottom surface 608 to a predetermined length along grasper portion 602. Grasper portion 602 can include external threads 612 (see FIG. 20).

Grasper sleeve 604 can be positioned around grasper portion 602, as shown in FIGS. 19 and 21. Grasper sleeve 604 can have internal threads (not shown) that correspond to external threads 612 (see FIG. 20) of grasper portion 602, thereby threadingly mating grasper portion 602 and grasper sleeve 604 to permit grasper sleeve 604 to advance and withdraw on and with respect to grasper portion 602. Grasper sleeve 604 can be generally elongate and can include an end portion generally designated 616.

In use, as illustrated in FIG. 19, the surgeon can position plate puller device 600 in communication with fastener 10. Head portion 606 of grasper portion 602 can be positioned over head section 40 of fastener 10 such that bottom surface 608 abuts first outer surface 62 of fastener receiving member 60. Screwdriver 610 can engage head section 40 of fastener 10. Head portion 606 of grasper portion 602 can be compressed or tightened around head section 40 of fastener 10 by advancing grasper sleeve 604 forwardly along grasper portion 602 toward head portion 606 of grasper portion 602.

In aspects where external threads 612 (see FIG. 20) are provided on grasper portion 602, grasper sleeve 604 can be forwardly advanced toward fastener receiving member 60 by rotating grasper sleeve 604 in relation to grasper portion 602. End portion 616 of grasper sleeve 604 can contact and engage head portion 606 of grasper portion 602. Upon contacting head portion 606 with end portion 616, the surgeon can continue to advance grasper sleeve 604 such that wedges 608 (see FIG. 20) can compress to fit tightly around head section 40 of fastener 10, thereby preventing head section 40 of fastener 10 from advancing within aperture A of fastener receiving member 60. Slits 614 can aid in facilitating compression of head portion 606 of grasper portion 602 around head section 40 of fastener 10.

The surgeon can advance elongate section 20 of fastener 10 further within bone B such that second outer surface 64 of fastener receiving member 60 can be pulled against bone surface BS. The surgeon can then withdraw end portion 616 of grasper sleeve 604 from head portion 606 of grasper portion 602 such that wedges 607 expand radially outwardly, thereby permitting head section 40 of fastener 10 to be inwardly advanced within aperture A to engage contact region 85 in a locking manner. In aspects where external threads 612 are provided on grasper portion 602, the surgeon can reverse the rotation of grasper sleeve 604 to withdraw end portion 616 from wedges 607, thereby relieving compression of wedges 607. As such, fastener receiving member 60 can be pulled against bone surface BS to prevent an undesirable "stand off" position in which gap 700 is present between second outer surface 64 of fastener receiving member 60 and bone surface BS.

It will be understood that various details of the present disclosure may be changed without departing from the scope of the present disclosure. Furthermore, the foregoing description is for the purpose of illustration only, and not for the purpose of limitation, as the present disclosure is defined by the claims as set forth hereinafter.

What is claimed is:

1. A surgical plate-pulling system that facilitates pulling a fastener receiving member against a bone surface, comprising:
   (a) a fastener comprising an elongate section and an adjoining head section disposed along a fastener axis, the head section comprising a thread;
   (b) a fastener receiving member comprising first and second opposing major surfaces, an inside surface extending between the first and second major surfaces and defining an aperture generally coaxially disposed about an aperture axis, and a tappable contact region disposed on the inside surface; and
   (c) a plate puller device including a grasper portion that is configured to fit around a screwdriver, and a grasper sleeve positioned around the grasper portion, the plate puller device configured for facilitating the fastener receiving member to be pulled against a bone surface during insertion of the fastener therethrough by preventing the head section of the fastener from engaging the tappable contact region of the fastener receiving member until the fastener receiving member is pulled against the bone surface by the grasper portion and grasper sleeve being in cooperative engagement such that the grasper portion grips the head section of the fastener to prevent the head section of the fastener from advancing within the aperture of the fastener receiving member wherein the fastener is a surgical bone screw, the fastener receiving member is a surgical bone plate, the head portion of the grasper portion comprises a plurality of radially displaceable wedges and the grasper sleeve may be advanced against the plurality of radially displaceable wedges such that the plurality of radially displaceable wedges compress around the head section of the fastener, thereby preventing the head section of the fastener from advancing within the fastener receiving member, and each wedge comprises a triangular wedge shaped cross-section with a flat bottom surface for preventing the head section of the fastener from engaging the fastener receiving member by the flat bottom surface abutting against the fastener receiving member to pull the fastener receiving member toward the bone surface.

2. The system according to claim 1, wherein the plate puller device comprises a screwdriver.

3. The system according to claim 1, wherein the grasper portion has a threaded section.

* * * * *